(12) United States Patent
Lee et al.

(10) Patent No.: US 10,906,949 B2
(45) Date of Patent: Feb. 2, 2021

(54) METHODS OF TREATING SPINAL CORD INJURY USING A CHONDROITIN SULFATE PROTEOGLYCAN (CSPG) REDUCTION PEPTIDE (CRP) COMPRISING A CELL MEMBRANE PENETRATING DOMAIN, A CSPG BINDING DOMAIN, AND A LYSOSOME TARGETING DOMAIN

(71) Applicant: The Cleveland Clinic Foundation, Cleveland, OH (US)

(72) Inventors: Yu-Shang Lee, Solon, OH (US); Ching-Yi Lin, Solon, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 16/626,940

(22) PCT Filed: Jun. 26, 2018

(86) PCT No.: PCT/US2018/039539
§ 371 (c)(1),
(2) Date: Dec. 27, 2019

(87) PCT Pub. No.: WO2019/005822
PCT Pub. Date: Jan. 3, 2019

(65) Prior Publication Data
US 2020/0131237 A1  Apr. 30, 2020

Related U.S. Application Data

(60) Provisional application No. 62/526,160, filed on Jun. 28, 2017.

(51) Int. Cl.
| | | |
|---|---|---|
| *A61K 38/00* | (2006.01) | |
| *A61K 49/00* | (2006.01) | |
| *C07K 14/00* | (2006.01) | |
| *A61K 38/17* | (2006.01) | |
| *A61K 38/18* | (2006.01) | |
| *C07K 14/475* | (2006.01) | |

(Continued)

(52) U.S. Cl.
CPC ........ *C07K 14/4703* (2013.01); *A61K 9/0019* (2013.01); *A61K 31/727* (2013.01); *A61P 25/00* (2018.01); *A61P 25/28* (2018.01); *C07K 19/00* (2013.01); *A61K 31/737* (2013.01); *A61K 38/00* (2013.01); *A61K 38/16* (2013.01); *A61K 38/1709* (2013.01); *A61K 38/39* (2013.01); *A61K 47/42* (2013.01); *A61K 47/64* (2017.08); *A61K 47/645* (2017.08); *A61K 48/005* (2013.01); *A61K 49/0056* (2013.01); *A61K 49/14* (2013.01); *A61K 2039/55516* (2013.01); *A61K 2039/6031* (2013.01); *A61K 2121/00* (2013.01); *A61K 2300/00* (2013.01); *A61L 27/22* (2013.01); *A61L 2300/236* (2013.01); *A61L 2300/252* (2013.01); *A61L 2430/32* (2013.01); *A61P 17/02* (2018.01); *C07K 2319/03* (2013.01); *C07K 2319/70* (2013.01); *C07K 2319/95* (2013.01); *G01N 33/5058* (2013.01); *G01N 33/68* (2013.01)

(58) Field of Classification Search
CPC .. A61K 38/00; A61K 2300/00; A61K 48/005; A61K 38/16; A61K 49/0056; A61K 51/088; A61K 2039/55516; A61K 2039/6031; A61K 38/1709; A61K 31/727; A61K 31/737; A61K 38/177; A61K 38/39; A61K 47/64; A61K 49/14; A61K 47/42; A61K 47/645; A61K 2121/00; C07K 2319/00; C07K 14/00; C07K 14/47; C07K 14/4702; C07K 2319/03; C07K 19/00; C07K 2319/01; C07K 2319/06; C07K 2319/10; C07K 2319/70; C07K 2319/95; G01N 33/5058; G01N 33/68; G01N 33/6869; Y02A 90/26; A61P 9/10; A61P 25/28; A61P 25/00; A61P 17/02; C12N 5/0612; A61B 2018/00434; A61B 2018/0044; A61N 2007/0021

See application file for complete search history.

(56) References Cited

U.S. PATENT DOCUMENTS 8,207,316 B1 * 6/2012 Bentwich ................. A61P 31/00
536/23.1
9,744,188 B2 * 8/2017 Flanagan ............. A61K 38/177
(Continued)

FOREIGN PATENT DOCUMENTS

| WO | WO2012/112953 | * | 8/2012 |
| WO | WO2014/047741 | * | 4/2014 |
| WO | WO 2017/079723 | | 5/2017 |

OTHER PUBLICATIONS

Blight Nat. Neurosci. 2002. 5: 1051-4.*
(Continued)

*Primary Examiner* — Chang-Yu Wang
(74) *Attorney, Agent, or Firm* — Casimir Jones, S.C.; Jason R. Bond

(57) ABSTRACT

Provided herein are compositions, systems, kits, and methods for treating nervous system injuries caused by trauma or neurodegeneration or aging in a subject by administering a CSPG or SOCS3 reduction peptide (CRP and SRP respectively), or a nucleic acid sequence encoding the CRP or SRP, wherein both the CRP and SRP comprise a cell membrane penetrating domain, and a lysosome targeting domain, and the CRP further comprises a chondroitin sulfate proteoglycan (CSPG) binding domain, and the SRP further comprises a suppressor of cytokine signaling-3 (SOCS3) binding domain.

10 Claims, 39 Drawing Sheets
Specification includes a Sequence Listing.

(51) Int. Cl.

| | |
|---|---|
| *C07K 14/48* | (2006.01) |
| *C07K 14/47* | (2006.01) |
| *A61P 25/00* | (2006.01) |
| *A61K 9/00* | (2006.01) |
| *A61P 25/28* | (2006.01) |
| *C07K 19/00* | (2006.01) |
| *A61K 31/727* | (2006.01) |
| *A61K 38/16* | (2006.01) |
| *A61K 39/00* | (2006.01) |
| *A61P 17/02* | (2006.01) |
| *G01N 33/50* | (2006.01) |
| *G01N 33/68* | (2006.01) |
| *A61K 47/64* | (2017.01) |
| *A61K 49/14* | (2006.01) |
| *A61K 31/737* | (2006.01) |
| *A61K 38/39* | (2006.01) |
| *A61K 48/00* | (2006.01) |
| *A61K 47/42* | (2017.01) |
| *A61L 27/22* | (2006.01) |

(56) References Cited

U.S. PATENT DOCUMENTS

| | | | | |
|---|---|---|---|---|
| 10,287,333 B2* | 5/2019 | Wang | ........................ | A61P 25/16 |
| 2002/0177207 A1* | 11/2002 | Sugiyama | ............... | C07K 14/47 |
| | | | | 506/3 |
| 2004/0029114 A1* | 2/2004 | Mack | ................... | C07K 14/47 |
| | | | | 435/6.14 |
| 2004/0156826 A1* | 8/2004 | Dangond | ............... | A61K 31/00 |
| | | | | 424/93.2 |
| 2005/0222029 A1* | 10/2005 | Bartel | ................. | C07K 14/775 |
| | | | | 530/359 |
| 2007/0065415 A1* | 3/2007 | Kleinsek | ................ | A61K 35/12 |
| | | | | 424/93.7 |
| 2007/0276126 A1* | 11/2007 | Elliott | ................... | C07K 14/705 |
| | | | | 530/350 |
| 2009/0082265 A1* | 3/2009 | Bartel | ................ | A61K 31/7052 |
| | | | | 514/1.2 |
| 2009/0169573 A1* | 7/2009 | Schultz | ................... | A61P 35/00 |
| | | | | 424/185.1 |
| 2013/0065267 A1 | 3/2013 | Mao | | |
| 2014/0045762 A1* | 2/2014 | Flanagan | ............... | A61K 45/06 |
| | | | | 514/17.7 |
| 2015/0266935 A1* | 9/2015 | Wang | .................... | A61K 31/00 |
| | | | | 514/17.8 |
| 2015/0299687 A1 | 10/2015 | Gruskin et al. | | |
| 2018/0327462 A1* | 11/2018 | Matouschek | ........ | C07K 14/435 |
| 2019/0040378 A1* | 2/2019 | Fotin-Mleczek | ........................... | |
| | | | | C07K 14/70521 |
| 2019/0211070 A1* | 7/2019 | Wang | ..................... | A61P 25/28 |

OTHER PUBLICATIONS

Schmidt et al. Annu. Rev. Biomed. Eng. 2003. 5: 293-347.*
Hoke et al. Nat. Clin. Pract. Neurol. 2006: 448-454.*
'T Hart et al. Curr. Opin. Neurol. 2003. 16: 375-383.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Potashikin et al., Parkinson's Disease, 2011; 658083; doi:104061/2011/658083.*
Tayebati, Mech. Ageing Dev. 2006. 127.*
Sarter, Neurosci. and Biobehav. Rev. 2004. 28: 645-650.*
Falkenburger et al., J. Neural. Transm, 2006; 70:261-268.*
Henstridge et al. Nat. Rev. Neurosci. 2019; 20: 94-107.*
Swerdlow, Clin. Interv. Ageing 2007; 2:347-359.*
Atwood et al., J. Alzheimer's Disease; 2015; 47:33-47.*
Anger. Neurotoxicology 1991. 12: 403-13.*
Moore et al., Annu. Rev. Neurosci. 2005; 28:57-87.*
Jagmag et al., Front. Neurosci. 2016; 9:503. Doi:10.3389/fnins.2015.00503.*
Aricescu et al., Heparan Sulfate Proteoglycans Are Ligands for Receptor Protein Tyrosine Phosphatase sigma. Mol Cell Biol. Mar. 2002;22(6):1881-92.
Keough et al., An Inhibitor of Chondroitin Sulfate Proteoglycan Synthesis Promotes Central Nervous System Remyelination. at Commun . Apr. 26, 2016;7:11312.
Shen et al., PTPsigma Is a Receptor for Chondroitin Sulfate Proteoglycan, an Inhibitor of Neural Regeneration. Science. Oct. 23, 2009;326(5952):592-6.
ISR and Written Opinion for PCT/US2018/039539 dated Nov. 19, 2018, 14 pages.

* cited by examiner

Experimental Design

1. Sub-acute treatment of CRP:

2. Chronic treatment of CRP:

BBB locomotion test: once a week after SCI
Voiding pattern test by metabolic cage: every two weeks after SCI

CRP improves bladder function after SCI
-- Assessment by Urodynamic analyses CRP treatment reduces residual volume and volume per void toward normal condition

CRP improves bladder function after SCI
-- Assessment by Urodynamic analyses CRP treatment reduces overactive bladder by the reduction of both the number and the amplitude of non-voiding contraction

METHODS OF TREATING SPINAL CORD INJURY USING A CHONDROITIN SULFATE PROTEOGLYCAN (CSPG) REDUCTION PEPTIDE (CRP) COMPRISING A CELL MEMBRANE PENETRATING DOMAIN, A CSPG BINDING DOMAIN, AND A LYSOSOME TARGETING DOMAIN

SEQUENCE LISTING

The text of the computer readable sequence listing filed herewith, titled "35302-252-Sequence-Listing_ST25", created Sep. 16, 2020, having a file size of 27,000 bytes, is hereby incorporated by reference in its entirety.

The present application is a § 371 U.S. National Entry Application of PCT/US2018/039539, which claims priority to U.S. Provisional application Ser. No. 62/526,160 filed Jun. 28, 2017, each of which is herein incorporated by reference in its entirety.

FIELD

Provided herein are compositions, systems, kits, and methods for treating nervous system injuries caused by trauma or neurodegeneration or aging in a subject by administering a CSPG or SOCS3 reduction peptide (CRP and SRP respectively), or a nucleic acid sequence encoding the CRP or SRP, wherein both the CRP and SRP comprise a cell membrane penetrating domain, and a lysosome targeting domain, and the CRP further comprises a chondroitin sulfate proteoglycan (CSPG) binding domain, and the SRP further comprises a suppressor of cytokine signaling-3 (SOCS3) binding domain.

BACKGROUND

There is a huge market desire to remove scares caused by trauma and/or neurodegeneration to facilitate nerve regrowth and to enhance functional outcomes in both Peripheral Nervous System (PNS) and Central Nervous System (CNS) clinically. There is currently no intervention available clinically to target the spinal cord injury (SCI) and to address its associated neurological disorders including bladder control. The patients with SCI in the U.S. have been estimated to be approximately 276,000 people, with a range from 240,000 to 337,000 persons in 2014. The new cases are about 13,000 per year. The bladder function is a high priority that patients with SCI would like to be returned.

There are two major approaches applied in experiments to reduce chondroitin sulfate proteoglycan (CSPG, the major component of scarring) are bacterial enzyme chondroitinase ABC and Lentiviral delivery of chondroitinase ABC. However, both chondroitinase ABC and Lentiviral delivery of chondroitinase ABC have only limited efficacy and are not clinically applicable. Chondroitinase ABC has low thermal stability, short longevity and must be applied locally. These disadvantages limit its efficacy and clinical application. Lentiviral delivery of chondroitinase ABC has a relatively low transfection rate, and biological safety concerns. In addition, Lentivirus needs to be applied about two weeks before injury/trauma. The timing and amount applied cannot be controlled. All of these disadvantages limit efficacy and clinical application of Lentiviral delivery of chondroitinase ABC.

Another newly published peptide, intracellular sigma peptide (ISP), was originally designed to interfere the function of one of the receptors of CSPG (i.e. PTPσ) in order to block the inhibitory effects of CSPG, but has no effects on CSPG itself in vivo. While ISP when applied immediately after SCI in rats has been reported to have minor effects on promoting functional recovery after SCI, the underlying mechanisms are still unknown even after extensive investigation for years. The most critical disadvantage of ISP is that ISP has no effects on chronic SCI when ISP was applied two-month after SCI. Such disadvantages and the unknown mechanisms underlying its published effects significantly limit the efficacy and clinical application of ISP.

SUMMARY

Provided herein are compositions, systems, kits, and methods for treating nervous system injuries caused by trauma or neurodegeneration or aging in a subject by administering a CSPG or SOCS3 reduction peptide (CRP and SRP respectively), or a nucleic acid sequence encoding the CRP or SRP, wherein both the CRP and SRP comprise a cell membrane penetrating domain, and a lysosome targeting domain, and the CRP further comprises a chondroitin sulfate proteoglycan (CSPG) binding domain, and the SRP further comprises a SOCS3 binding domain.

In certain embodiments, provided herein are methods of treating nervous system injury or trauma or degeneration or aging (e.g., advanced years, such as over 75 years old) in a subject comprising: administering a CSPG reduction peptide (CRP), or a nucleic acid sequence encoding the CRP, to a subject with a nervous system injury or trauma or degeneration or aging, wherein the CRP comprises: i) a first amino acid sequence encoding a cell membrane penetrating domain, ii) a second amino acid sequence encoding a chondroitin sulfate proteoglycan (CSPG) binding domain, and iii) a third amino acid sequence encoding a lysosome targeting domain.

In some embodiments, the nervous system injury or trauma or degeneration or aging is localized to at least one nervous system site on the subject (e.g., particular location between certain vertebrate on the spinal cord). In other embodiments, the administering is under conditions such that the CRP reduces the level of CSPG present at the at least one nervous system site (e.g., one site, two sites, three sites, etc.). In other embodiments, the nervous system site is in the spinal cord of the subject. In other embodiments, the nervous system site is in the degenerated brain and/or spinal cord of the subject. In further embodiments, the nervous system injury or trauma or degeneration or aging is to the subject's central nervous system (CNS). In some embodiments, the nervous system injury or trauma or degeneration or aging is to the subject's peripheral nervous system (PNS).

In certain embodiments, administering is conducted within about 24 hours of the nervous system injury or trauma or degeneration or aging (e.g., within 1 hour . . . 5 hours . . . 15 hours . . . 20 hours, or within 24 hours). In some embodiments, the administering is conducted after at least two days of the nervous system injury or trauma or degeneration or aging (e.g., after 2 days . . . 4 days . . . or 6 days). In other embodiments, the administering is conducted at least one week after the nervous system injury or trauma or degeneration or aging (e.g., after 7 days . . . 15 days . . . or 25 days). In further embodiments, the administering is conducted at least one month after the nervous system injury or trauma or degeneration or aging (e.g., at least one month or 1.5 months). In additional embodiments, the administering is conducted at least two months after nervous system injury or trauma or degeneration or aging (e.g., at least 2 months . . . 5 months . . . 1 year . . . 2 years . . . or 5 years after the injury or trauma).

In certain embodiments, provided herein are methods of treating multiple sclerosis (MS), or aiding in limb transplant, in a subject comprising: administering a CSPG reduction peptide (CRP), or a nucleic acid sequence encoding the CRP, to a subject with MS (or other neurological condition) or undergoing limb transplant, wherein the CRP comprises: i) a first amino acid sequence encoding a cell membrane penetrating domain, ii) a second amino acid sequence encoding a chondroitin sulfate proteoglycan (CSPG) binding domain, and iii) a third amino acid sequence encoding a lysosome targeting domain.

In some embodiments, provided herein are compositions, systems, and kits comprising: a CSPG reduction peptide (CRP) (e.g., to reduce scars), or a nucleic acid sequence encoding the CRP, wherein the CRP comprises: a) a first amino acid sequence encoding a cell membrane penetrating domain, b) a second amino acid sequence encoding a chondroitin sulfate proteoglycan (CSPG) binding domain, and c) a third amino acid sequence encoding a lysosome targeting domain. In particular embodiments, the compositions, systems, further comprise a device for injecting a composition comprising the CRP into a subject's nervous system.

In particular embodiments, the first amino acid sequence is located at the N-terminal or C-terminal of the CRP. In other embodiments, the third amino acid sequence is located at the N-terminal or C-terminal of the CRP. In additional embodiments, the second amino acid sequence is located between the first and third amino acid sequences. In further embodiments, the first amino acid sequence comprises or consists of an amino acid sequence shown in SEQ ID NOS: 1 and 5-27, or a sequence with one amino acid addition, subtraction or substitution. In additional embodiments, the third amino acid sequence comprises or consists of an amino acid sequence shown in SEQ ID NOS: 2 or 28-36, or a sequence with one amino acid addition, subtraction or substitution. In additional embodiments, the second amino acid sequence comprises or consists of an amino acid sequence shown in SEQ ID NO: 2 or 37-53, or a sequence with one amino acid addition, subtraction or substitution.

In certain embodiments, provided herein are methods of treating nervous system injury or trauma or degeneration or aging (e.g., older than 75 . . . 85 . . . or 95) in a subject comprising: administering a SOCS3 reduction peptide (SRP), or a nucleic acid sequence encoding the SRP, to a subject with a nervous system injury or trauma or degeneration or aging, wherein the SRP comprises: i) a first amino acid sequence encoding a cell membrane penetrating domain, ii) a second amino acid sequence encoding a Suppressor of cytokine signaling 3 (SOCS3) binding domain, and iii) a third amino acid sequence encoding a lysosome targeting domain.

In some embodiments, the nervous system injury or trauma or degeneration or aging is localized to at least one nervous system site on the subject (e.g., particular location between certain vertebrate on the spinal cord). In other embodiments, the administering is under conditions such that the SRP reduces the level of SOCS3 present at the at least one nervous system site (e.g., one site, two sites, three sites, etc.). In other embodiments, the nervous system site is in the spinal cord of the subject. In other embodiments, the nervous system site is in the degenerated brain and/or spinal cord of the subject. In further embodiments, the nervous system injury or trauma or degeneration or aging is to the subject's central nervous system (CNS). In some embodiments, the nervous system injury or trauma or degeneration or aging is to the subject's peripheral nervous system (PNS).

In certain embodiments, administering is conducted within about 24 hours of the nervous system injury or trauma or degeneration or aging (e.g., within 1 hour . . . 5 hours . . . 15 hours . . . 20 hours, or within 24 hours). In some embodiments, the administering is conducted after at least two days of the nervous system injury or trauma or degeneration or aging (e.g., after 2 days . . . 4 days . . . or 6 days). In other embodiments, the administering is conducted at least one week after the nervous system injury or trauma or degeneration or aging (e.g., after 7 days . . . 15 days . . . or 25 days). In further embodiments, the administering is conducted at least one month after the nervous system injury or trauma or degeneration or aging (e.g., at least one month or 1.5 months). In additional embodiments, the administering is conducted at least two months after nervous system injury or trauma or degeneration or aging (e.g., at least 2 months . . . 5 months . . . 1 year . . . 2 years . . . or 5 years after the injury or trauma).

In certain embodiments, provided herein are methods of treating multiple sclerosis, motor neuron disease (MND), ALS, or aiding in limb transplant, in a subject comprising: administering a SOCS3 reduction peptide (SRP), or a nucleic acid sequence encoding the SRP, to a subject with MND (or other neurological condition) or undergoing limb transplant, wherein the SRP comprises: i) a first amino acid sequence encoding a cell membrane penetrating domain, ii) a second amino acid sequence encoding SOCS3 binding domain, and iii) a third amino acid sequence encoding a lysosome targeting domain.

In some embodiments, provided herein are compositions, systems, and kits comprising: a SOCS3 reduction peptide (SRP) (e.g., to reduce scars), or a nucleic acid sequence encoding the SRP, wherein the SRP comprises: a) a first amino acid sequence encoding a cell membrane penetrating domain, b) a second amino acid sequence encoding a SOCS3 binding domain, and c) a third amino acid sequence encoding a lysosome targeting domain. In particular embodiments, the compositions, systems, further comprise a device for injecting a composition comprising the SRP into a subject's nervous system.

In particular embodiments, the first amino acid sequence is located at the N-terminal or C-terminal of the SRP. In other embodiments, the third amino acid sequence is located at the N-terminal or C-terminal of the SRP. In additional embodiments, the second amino acid sequence is located between the first and third amino acid sequences. In further embodiments, the first amino acid sequence comprises or consists of an amino acid sequence shown in SEQ ID NOS: 1 and 5-27, or a sequence with one amino acid addition, subtraction or substitution. In additional embodiments, the third amino acid sequence comprises or consists of an amino acid sequence shown in SEQ ID NOS: 2 or 28-36, or a sequence with one amino acid addition, subtraction or substitution. In additional embodiments, the second amino acid sequence comprises or consists of an amino acid sequence shown in SEQ ID NO: 54-89, or a sequence with one amino acid addition, subtraction or substitution.

DESCRIPTION OF THE FIGURES

FIG. 19 (F and G) also shows SRP treatment improved bursting activities of external urethral sphincter (EUS) recorded by electromyogram (EMG) after T8 contusive SCI. EUS EMG recording were conducted 3 months post-SCI. The EUS EMG during the void period showed improvement in bursting activity indicated by red rectangle following SRP (G) when compared to the scrambled peptide (scrambled) group (F).

FIG. 25 shows that CRP significantly reduces CSPG produced by Neu7 cells to a comparable level what ChABC does. Note there is also a dosage response by CRP application.

FIG. 26 shows Kinematics assessment in SCI rats. (A) Representative total of hindlimb movement trajectories for spinal-intact, SCI+scrambled peptide (scr) and SCI+CRP groups at 3 months post-SCI. (B-G) CRP treatment significantly improved several parameters of gait pattern with trajectories more consistent to what the spinal-intact animals did, when compared to scr treatment.

FIG. 31 shows BBB scores that show that CRP treatment improves hindlimb locomotion after chronic SCI (N=6 to 8 animals per group). Note the significant increases in BBB locomotion scale by CRP at 5 months post SCI when compared to what at the time (two months post SCI) of beginning treatment.

FIG. 32 shows representative 2D trajectory patterns indicated CRP treatment improved stepping kinematic of both hindlimbs by CRP at 5 months post SCI when it compared to what at the time (two months post SCI) of beginning treatment.

FIG. 33 shows representative cystometrograms (CMG) data indicated 3 months of CRP treatment (starting at 2 months post SCI) can reduce hyperactive bladder and improve other CMG parameters.

FIG. 34 shows representative urodynamic and external urethral sphincter (EUS) electromyogram (EMG) recordings indicated CRP treatment can improve EUS bursting activity during the void period when compared to the scrambled peptide application after chronic SCI. The box area indicates the bursting activity.

FIG. 35 shows representative spinal cord transverse images that CRP treatment can enhance 5HT+ nerve fibers sprouting in lumbosacral level when compared to the scrambled peptide treatment after chronic SCI.

FIG. 36 shows 5HT immunoreactivity in lumbosacral level after chronic SCI. Representative spinal cord transverse images show that low amount of 5HT fibers found at L4 levels after contusive SCI, while CRP treatment significantly increases immunoreactivity of 5HT fibers. Representative images with double staining of WFA and 5HT shows areas with robustly decreased PNN (indicated by WFA+) but enhanced 5-HT sprouting.

FIG. 37 shows the acute treatment of CRP with allograft of a peripheral nerve segment (2 cm) improved the stepping performance of hindlimbs at 3 months after complete sciatic nerve transection. The representative 2D trajectory and improved kinematics parameters indicated CRP treated animals improved the stepping more toward to what the uninjured limb did, while compared to the vehicle treated animals. The CRP was delivered through subcutaneous injection near the injured site (once per day) staring immediately after surgery for 3 months.

DETAILED DESCRIPTION

Figure 1:
FIG. 1 shows a schematic of the exemplary CRP employed in Example 1.

Provided herein are compositions, systems, kits, and methods for treating nervous system injuries caused by trauma or neurodegeneration or aging in a subject by administering a CSPG or SOCS3 reduction peptide (CRP and SRP respectively), or a nucleic acid sequence encoding the CRP or SRP, wherein both the CRP and SRP comprise a cell membrane penetrating domain, and a lysosome targeting domain, and the CRP further comprises a chondroitin sulfate proteoglycan (CSPG) binding domain, and the SRP further comprises a SOCS3 binding domain.

Chondroitin sulfate proteoglycans (CSPGs) are the major components of scar, which are significantly increased after injury/trauma to both peripheral nervous system (PNS) and central nervous system (CNS). However, there is no clinically applicable strategy to reduce CSPGs now. The CSPG reduction peptides (CRPs), and nucleic acid sequences encoding CRPs, provide an effective way to remove CSPGs from the site of injury caused by trauma or neurodegeneration or aging to CNS and PNS. The benefits of removing CSPGs after injury include promoting the regrowth of damaged nerves and enhancing functional outcomes.

In certain embodiments, the CRP has the following sequence: N-YGRKKRRQRRR-PKPRVTWNKKGKKVNSQRF-KFERQKILDQRFFE-C (SEQ ID NO:4). One of skill in the art could construct a corresponding nucleic acid sequence based on the known codon triplets for the amino acids specified in SEQ ID NO:4. The SEQ ID NO:4 sequence has the following three components:

```
Cell membrane penetrating domain:
YGRKKRRQRRR;              (SEQ ID NO: 1)

Central CSPG binding domain:
PKPRVTWNKKGKKVNSQRF;      (SEQ ID NO: 3)
and

Lysosome targeting domain:
KFERQKILDQRFFE.           (SEQ ID NO: 2)
```

In certain embodiments, the SRP has the following sequence:

```
N-terminal cell membrane penetrating domain:
YGRKKRRQRRR;              (SEQ ID NO: 1)

Central CSPG binding domain from PTP sigma:
VQpYSTVVHS;               (SEQ ID NO: 54)
and C-terminal lysosome targeting domain:
KFERQKILDQRFFE.           (SEQ ID NO: 2)
```

Each of these domains may be constructed with longer, shorter, or mutated versions of the sequences shown in SEQ ID NOS: 1-3 and 54. For example, one could change one, two, three amino acids in these sequences. For example, one could make conservative changes to a particular amino acid sequence. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, and asparagine-glutamine. In certain embodiments, provided herein are peptides that have substantial identity to at least a portion of the amino acid sequences shown in SEQ ID NOs:1-89.

In certain embodiments, the N-terminal cell-membrane penetrating domain of a CRP or SRP is an amino acid sequence as shown in SEQ ID NOs: 1 and 5-27 of Table 1 or such a peptide with one, two, or three (or more) N-terminal or C-terminal additions, subtractions or mutations therein. One of skill in the art could construct a corresponding nucleic acid sequence based on the known codon triplets for the amino acid sequences shown in Table 1.

TABLE 1

| | Amino acid (AA) sequences | SEQ ID NO: |
|---|---|---|
| HIV-1 Tat-(47-57) | YGRKKRRQRRR | 1 |
| HIV-1 Tat-(47-57)-C | YGRKKRRQRRR-C | 5 |
| HIV-1 Tat-(47-57)-GC | YGRKKRRQRRR-GC | 6 |
| CA-HIV-1 Tat-(47-57) | CA-YGRKKRRQRRR | 7 |
| HIV-1 Tat-(47-57) 3x | YGRKKRRQRRRYGRKKRRQRRRYGRKKRRQRRR | 8 |

TABLE 1-continued

| Amino acid (AA) sequences | | SEQ ID NO: |
|---|---|---|
| HIV-1 Tat-(48-57) | GRKKRRQRRR | 9 |
| HIV-1 Tat-(48-57)-G | GRKKRRQRRR-G | 10 |
| HIV-1 Tat-(48-57)-CG | GRKKRRQRRR-CG | 11 |
| HIV-1 Tat-(48-59) | GRKKRRQRRRPP | 12 |
| HIV-1 Tat-(48-60) | GRKKRRQRRRPPQ | 13 |
| HIV-1 Tat-(48-60)-C | GRKKRRQRRRPPQ-C | 14 |
| HIV-1 Tat-(49-57) | RKKRRQRRR | 15 |
| D-Tat (49-57) | rkkrrqrrr | 16 |
| Retro-Tat (57-49) | RRRQRRKKR | 17 |
| D-Retro-Tat (57-49) | rrrqrrkkr | 18 |
| R9-TAT | GRRRRRRRRRPPQ | 19 |
| HIV-1 Rev-(34-50) | TRQARRNRRRRWRERQR-GC | 20 |
| HTLV-II Rex-(4-16) | TRRQRTRRARRNRGC | 21 |
| CCMV Gag-(7-25) | KLTRAQRRAAARKNKRNTR-GC | 22 |
| FHV coat-(35-49) | RRRRNRTRRNRRRVR | 23 |
| Arg6 | RRRRRR-GC | 24 |
| Arg8 | RRRRRRRR-GC | 25 |
| Pep-1 | KETWW-ETWWTEWSQPKKKRKV | 26 |
| Antp-(43-58) | RQIKIWFQNRRMKWKK | 27 |

In other embodiments, the cell membrane penetrating peptide is a protein transduction domain (PTD) with the presence of multiple arginine (R) residues as shown in SEQ ID NOs: 1 and 5-27 of Table 1. In other embodiments, the cell membrane penetrating peptide is a cell penetrating peptide (CPP) from the CPPsite 2.0, which is an updated version of database CPPsite. This site contains around 1700 unique cell penetrating peptides (CPPs) along with their secondary & tertiary structure, and can be found at www. followed by "crdd.osdd.net/raghava/cppsite/."

In certain embodiments, the C-terminal lysosomal targeting domain of a CRP or SRP is an amino acid sequence as shown in SEQ ID NOs: 2 and 28-36 of Table 2 or such a peptide with one, two, or three (or more) N-terminal or C-terminal additions, subtractions or mutations therein. In other embodiments, the lysosomal targeting domain is a chaperone-mediated autophagy (CMA)-targeting motif (CTM) containing a KFERQ-like motif, such as those shown in SEQ ID NOs: 2 and 28-36 of Table 2. One of skill in the art could construct a corresponding nucleic acid sequence based on the known codon triplets for the amino acid sequences shown in Table 2.

TABLE 2

| Amino acid (AA) sequences | SEQ ID NO: |
|---|---|
| KFERQKILDQRFFE | 2 |
| KFERQ-like | 28 |
| KFERQ | 29 |
| QKILD | 30 |
| QRFFE | 31 |
| KFERQKILD | 32 |
| QKILDQRFFE | 33 |
| KFERQRFFE | 34 |
| QRFFERQ | 35 |
| QRKFERQ | 36 |

In certain embodiments, the CSPG binding domain of a CRP is an amino acid sequence as shown in SEQ ID NOs: 3 and 37-53 of Table 3 or such a peptide with one, two, or three (or more) N-terminal or C-terminal additions, subtractions or mutations therein. One of skill in the art could construct a corresponding nucleic acid sequence based on the known codon triplets for the amino acid sequences shown in Table 3.

TABLE 3

| Amino acid (AA) sequences | SEQ ID NO: |
|---|---|
| PKPRVTWNKKGKKVNSQRF | 3 |
| KKGKK | 37 |
| NKKGKKV | 38 |
| NKKGKKVNS | 39 |
| KKGKKVNSQRF | 40 |
| RVTWNKKGKKVNSQR | 41 |
| PKPRVTWNKKGKKVNSQRFE | 42 |
| TGDPKPRVTWNKKGKKVNSQRF | 43 |
| TGDPKPRVTWNKKGKKVNSQRFE | 44 |
| PKPRVTWNRKGKKVNSQRF | 45 |
| PKPRVTWNRRGKKVNSQRF | 46 |
| PKPRVTWNRRGRKVNSQRF | 47 |
| PKPRVTWNRRGRRVNSQRF | 48 |
| PKPRVTWNKRGKKVNSQRF | 49 |
| PKPRVTWNKRGRKVNSQRF | 50 |
| PKPRVTWNKRGRRVNSQRF | 51 |

TABLE 3-continued

| Amino acid (AA) sequences | SEQ ID NO: |
|---|---|
| PKPRVTWNKKGRKVNSQRF | 52 |
| PKPRVTWNKKGRRVNSQRF | 53 |

In certain embodiments, the SOCS3 binding domain of a SRP is an amino acid sequence as shown in SEQ ID NOs: 54-89 of Table 4 or such a peptide with one, two, or three (or more) N-terminal or C-terminal additions, subtractions or mutations therein. One of skill in the art could construct a corresponding nucleic acid sequence based on the known codon triplets for the amino acid sequences shown in Table 4.

TABLE 4

SOCS3 binding domain peptides

| Amino acid (AA) sequences | SEQ ID NO: |
|---|---|
| V-Q-pY-S-T-V-V-H-S | 54 |
| V-Q-Y-S-T-V-V-H-S | 55 |
| V-E-pY-S-T-V-V-H-S | 56 |
| V-E-Y-S-T-V-V-H-S | 57 |
| V-X-pY-X-X-V-V-X | 58 |
| V-X-pY-X-X-L-V-X | 59 |
| V-X-pY-X-X-V-L-X | 60 |
| L-X-pY-X-X-V-V-X | 61 |
| V-X-pY-X-X-L-L-X | 62 |
| L-X-pY-X-X-V-L-X | 63 |
| L-X-pY-X-X-L-V-X | 64 |
| L-X-pY-X-X-L-L-X | 65 |
| V-X-Y-X-X-Y-V-X | 66 |
| V-X-Y-X-X-L-V-X | 67 |
| V-X-Y-X-X-V-L-X | 68 |
| L-X-Y-X-X-V-V-X | 69 |
| V-X-Y-X-X-L-L-X | 70 |
| L-X-Y-X-X-Y-L-X | 71 |
| L-X-Y-X-X-L-V-X | 72 |
| L-X-Y-X-X-L-L-X | 73 |
| V-X-pY-X-X-Y-V-X-S | 74 |
| V-X-pY-X-X-L-V-X-S | 75 |
| V-X-pY-X-X-V-L-X-S | 76 |
| L-X-pY-X-X-V-V-X-S | 77 |
| V-X-pY-X-X-L-L-X-S | 78 |
| L-X-pY-X-X-V-L-X-S | 79 |
| L-X-pY-X-X-L-V-X-S | 80 |
| L-X-pY-X-X-L-L-X-S | 81 |
| S-T-A-S-T-V-E-pY-S-T-V-V-H-S-G | 82 |
| S-T-A-S-T-V-E-pY-S-T-V-V-H-S | 83 |
| S-T-A-S-T-V-Q-pY-S-T-V-V-H | 84 |
| S-T-A-S-T-V-Q-pY-S-T-V-V | 85 |
| S-T-A-S-T-V-Q-pY-S-T-V-V-H-S-G | 86 |
| S-T-A-S-T-V-Q-pY-S-T-V-V-H-S | 87 |
| S-T-A-S-T-V-Q-pY-S-T-V-V-H | 88 |
| S-T-A-S-T-V-Q-pY-S-T-V-V | 89 | pY: phosphorylated tyrosine;
X: any amino acid

Work conducted during development of embodiments described herein demonstrate that injected SRP distributes to macrophages/microglia to be co-localized with lysosomes and SCI-upregulated SOCS3. SRP specifically and significantly reduces SOCS3, and it is associated with increased STAT3 activity. SRP treatment post-SCI significantly decreased pro-inflammatory responses, as indicated by decreased expression of both inducible nitric oxide synthase (iNOS) and TNF-α. Furthermore, SRP treatment significantly increased the amounts of TBK1 and the mitophagy adaptor optineurin, and enhanced phosphorylation of TBK1 and the mitophagy adaptor p62, as compared to treatment with scrambled peptide. Work conducted during development of embodiments described herein demonstrated that in a T8 contusion SCI model, SRP treatment significantly improves recovery of both locomotion and micturition three months after SCI.

EXAMPLES

Example 1

This Example describes treating spinal cord injury (SCI) in a model using a CSPG reduction peptide (CRP). The CRP had the following three components:

```
N-terminal cell membrane penetrating domain:
YGRKKRRQRRR;                (SEQ ID NO: 1)

Central CSPG binding domain from PTP sigma:
PKPRVTWNKKGKKVNSQRF;        (SEQ ID NO: 3)
and C-terminal lysosome targeting domain:
KFERQKILDQRFFE.             (SEQ ID NO: 2)
```

The full CRP sequence is as follows:

```
                            (SEQ ID NO: 4)
N - YGRKKRRQRRR-PKPRVTWNKKGKKVNSQRF-KFER-
QKILDQRFFE -
C.
```

The designed CRP (SEQ ID NO:4) includes an N-terminal cell membrane-penetrating domain (SEQ ID NO:1), a central CSPGs binding domain (SEQ ID NO:3), and a C-terminal lysosome targeting domain (SEQ ID NO:2) for directing the CRP-CSPGs complex to lysosomes for degradation. FIG. 1 shows a schematic of the exemplary CRP employed in this Example, as well as some of the benefits of such constructs.

Figure 2:
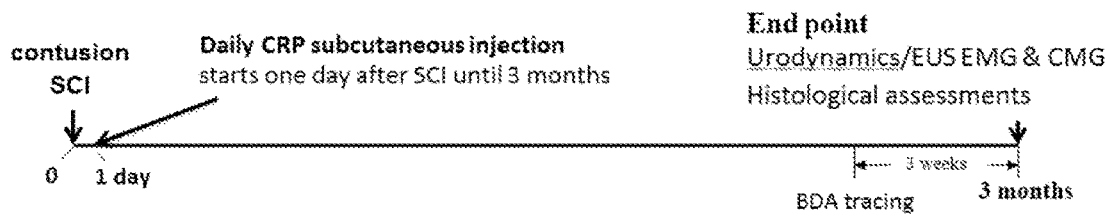
FIG. 2 shows a schematic of the experimental design for in vivo testing when a CRP was applied sub-acutely (one-day after SCI) or chronically (two-month after SCI) in Example 1.
Figure 2:
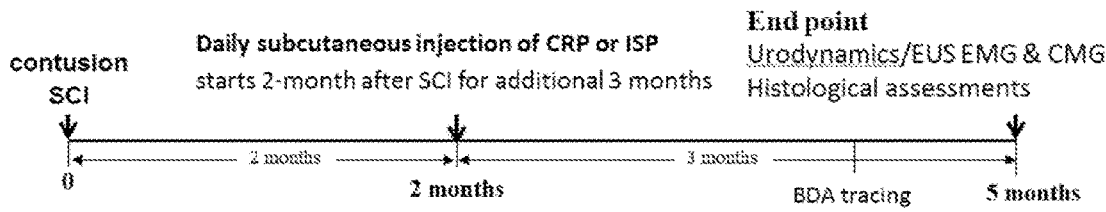

In this Example, the CRP has been applied in a preclinical rat model to test the efficacy of the treatment of spinal cord injury (SCI). The injury was made at thoracic 8 level using contusive injury device. The contusive SCI is the most clinical relevance among all experimental SCI models. We have assessed both motor and bladder control as functional outcomes and analyzed anatomical evidences to support these findings. We also selected sub-acute phase (ONE-DAY after SCI) and chronic phase (TWO-MONTHs after SCI) to start our treatment. FIG. 2 shows a schematic of the experimental design for the in vivo testing in this Example.

For the sub-acute treatment, continuous daily subcutaneous injection of CRP beginning one-day after SCI significantly reduces SCI-induced overexpression of CSPGs. Furthermore CRP can efficiently improve locomotion and bladder electromyography (EMG) activities and voiding patterns after SCI. Particularly, we found that CRP increases sprouting/regeneration of axons including serotonin (5-HT) and anterogradely traced fibers from brain stem and red nuclei, the critical pathways regulating both locomotion and bladder functions, below the SCI lesion and even in the lumbosacral spinal cord.

Figure 3:
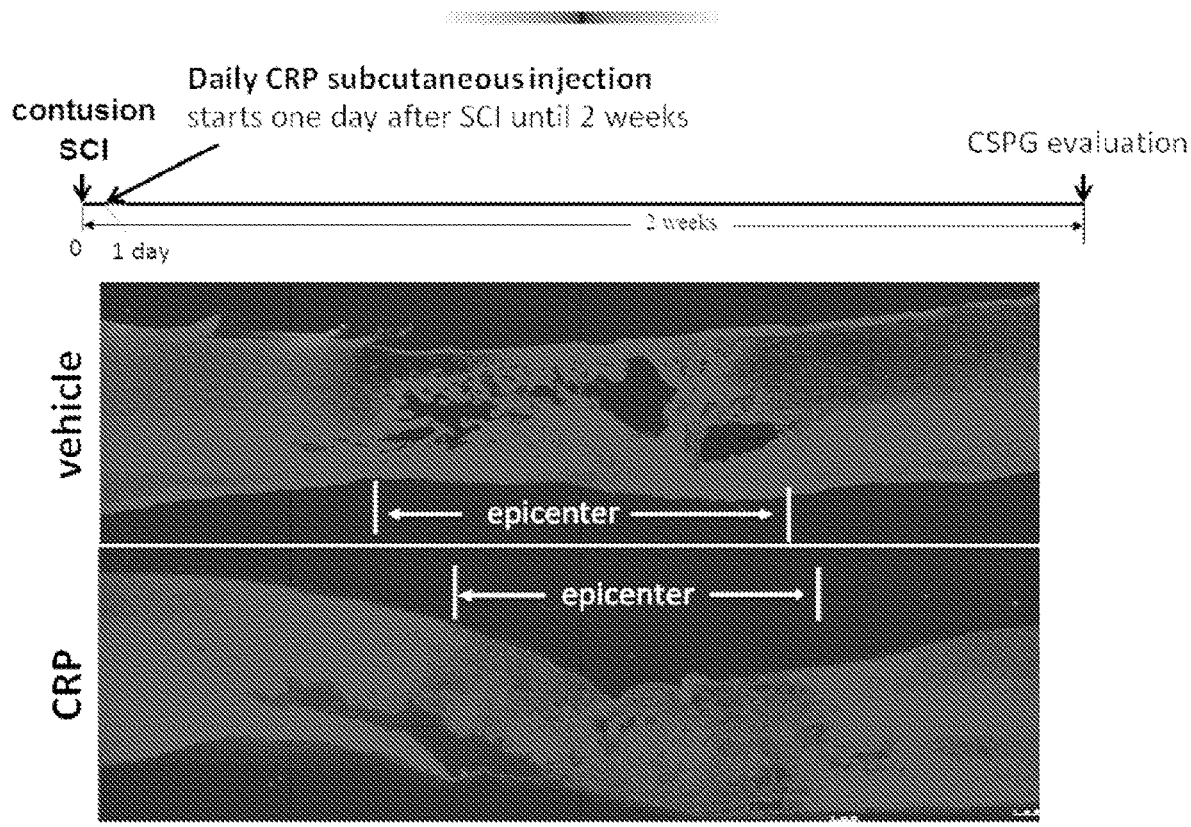
FIG. 3 shows histological results from the testing when CRP was applied sub-acutely in Example 1, where the CRP effectively decreased CSPG (the major component of scars) in lesion epicenter and adjacent tissue two weeks after SCI.
Figure 4:
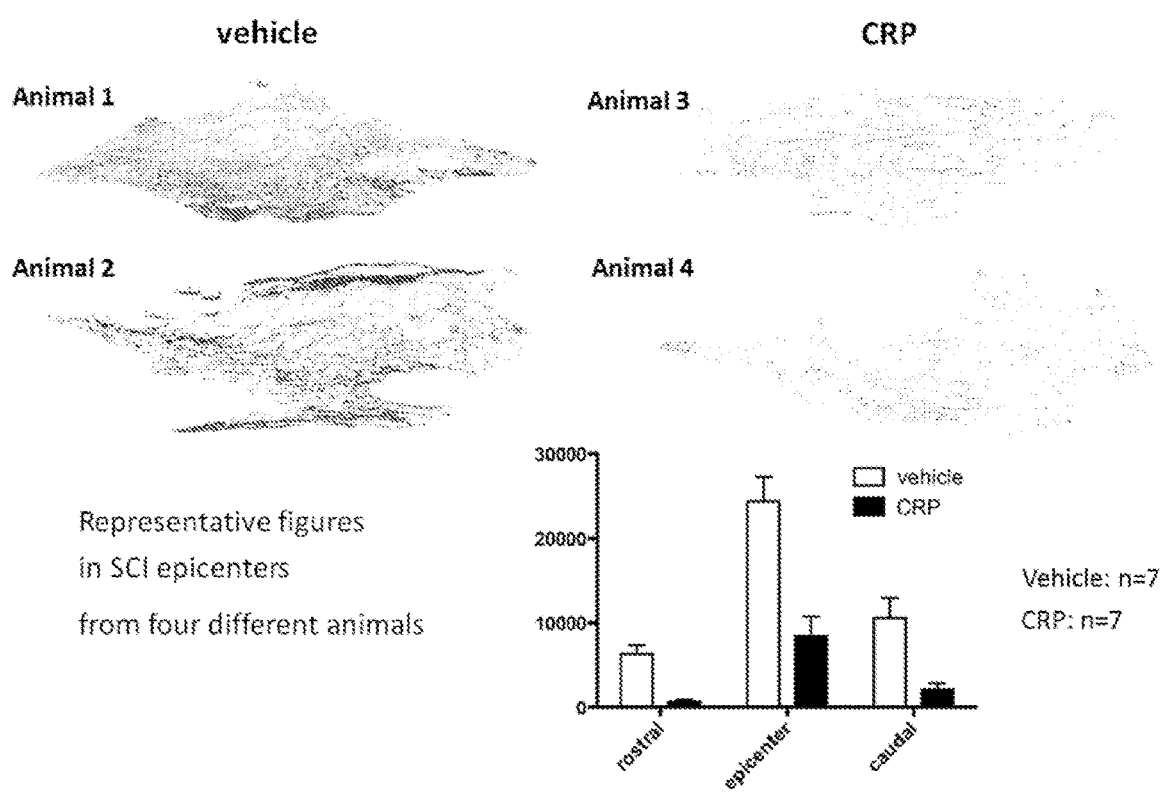
FIG. 4 shows results from the testing when CRP was applied sub-acutely, where the exemplary CRP significantly decreased CSPG three months after SCI.
Figure 5:
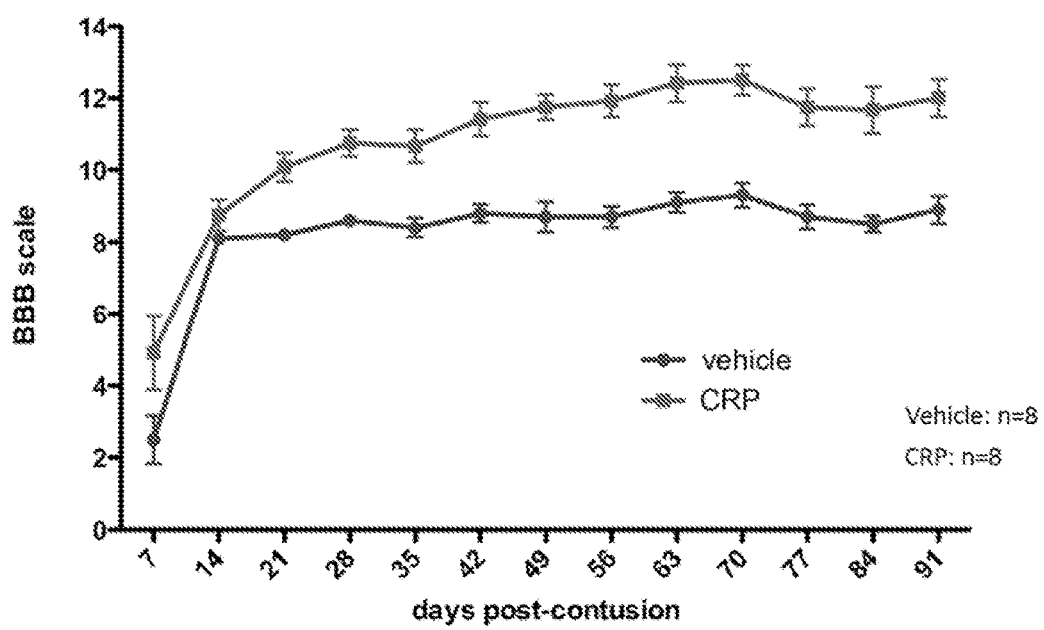
FIG. 5 shows results out to 91 days post-contusion shows that the CRP significantly promotes motor function recovery after SCI.
Figure 6:
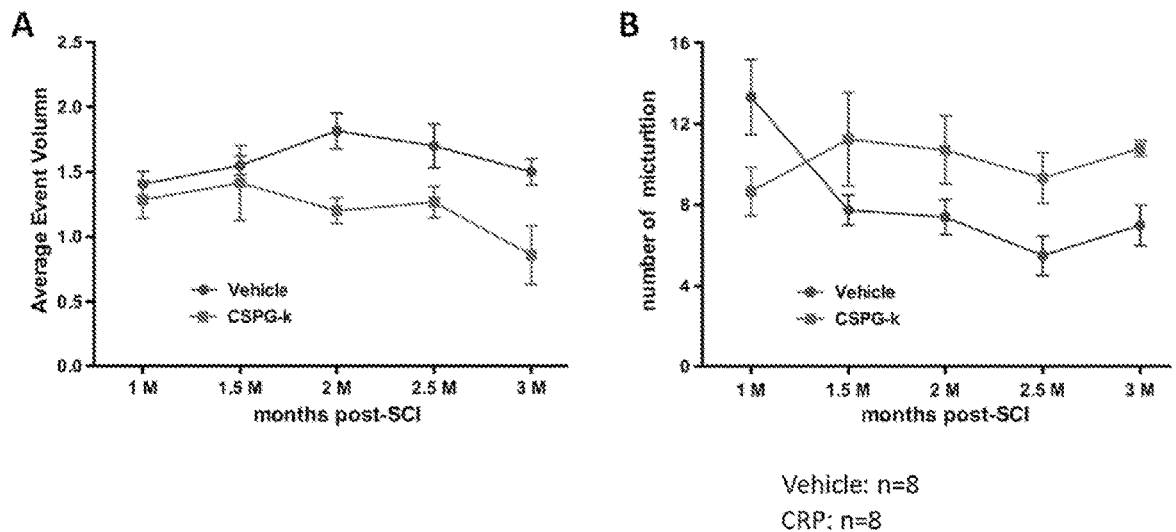
FIG. 6 shows that the CRP improves voiding patterns after SCI.
Figure 7:
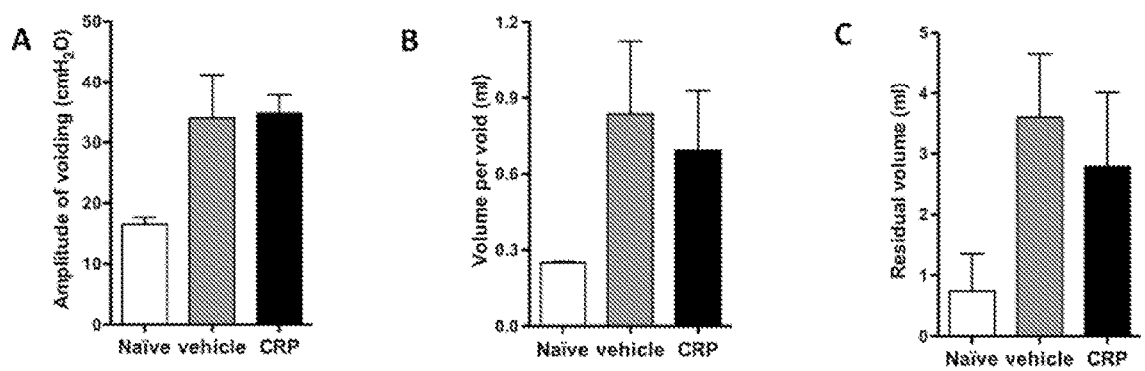
FIG. 7 shows that the CRP improves bladder function after SCI, reducing residual volume and volume per void toward normal condition.
Figure 8:
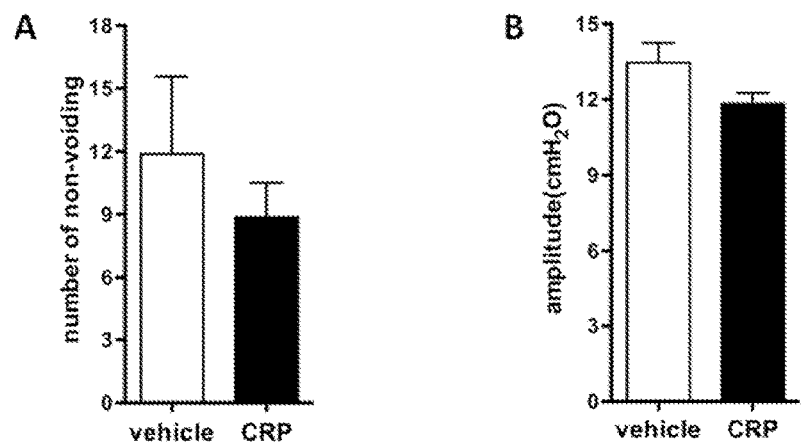
FIG. 8 shows that the CRP improves bladder function after SCI, reducing overactive bladder by the reduction of both the number and amplitude of non-voiding contraction.
Figure 9:
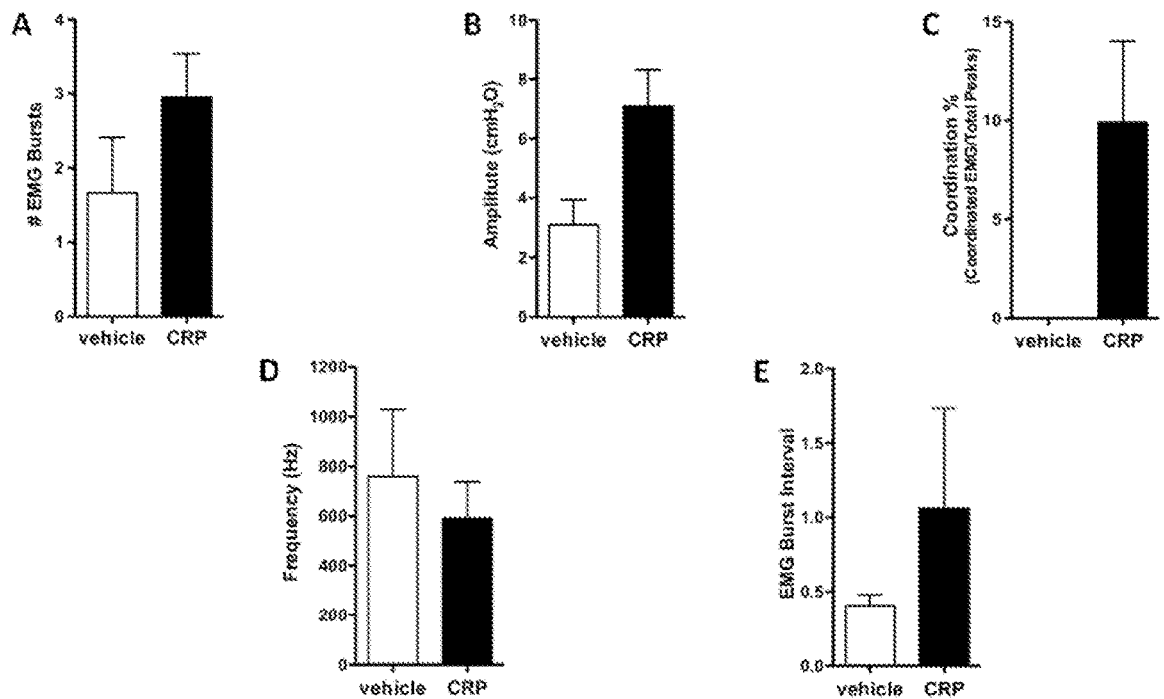
FIG. 9 shows that the CRP improves bladder function after SCI, improving external urethral sphincter (EUS) activity by increasing the number of burst, the EMG amplitude, and the coordination with detrusor contraction during the void period.
Figure 10:
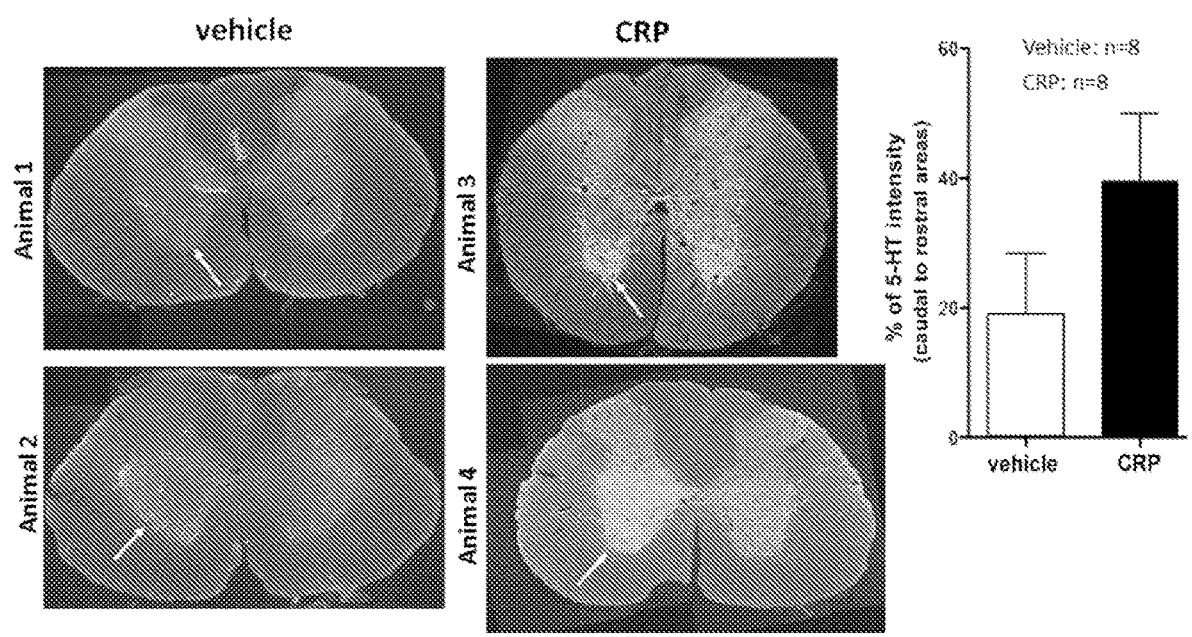
FIG. 10 shows the CRP enhances sprouting of serotonin (5-HT) fibers below lesion after SCI.
Figure 11:
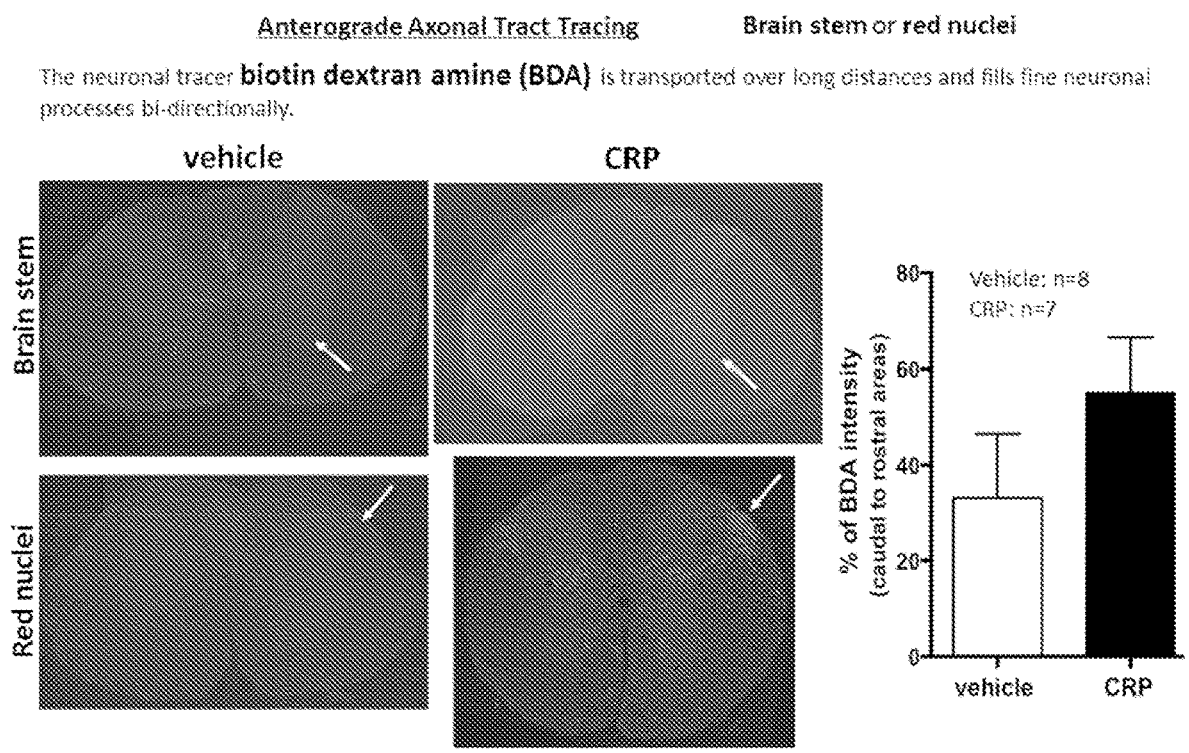
FIG. 11 shows that the CRP enhances nerve sprouting below lesion from neuron in brain stem and red nucleic after SCI.

The results of this testing are shown in the figures. In particular, FIG. 3 shows histological results from the sub-acute treatment, where CRP effectively decreased CSPG in lesion epicenter and adjacent tissue two weeks after SCI. FIG. 4 shows results from the sub-acute treatment, where CRP significantly decreased CSPG three months after SCI. FIG. 5 shows results out to 91 days post-contusion shows that CRP significantly promotes motor function recovery after SCI. FIG. 6 shows that CRP improves voiding patterns after SCI. FIG. 7 shows that CRP improves bladder function after SCI, reducing residual volume and volume per void toward normal condition. FIG. 8 shows that CRP improves bladder function after SCI, reducing overactive bladder by the reduction of both the number and amplitude of non-voiding contraction. FIG. 9 shows that CRP improves bladder function after SCI, improving external urethral sphincter (EUS) activity by increasing the number of burst, the EMG amplitude, and the coordination with detrusor contraction during the void period. FIG. 10 shows CRP enhances sprouting of serotonin (5-HT) fibers below lesion after SCI. FIG. 11 shows that CRP enhances nerve sprouting below lesion from neuron in brain stem and red nucleic after SCI.

Figure 12:
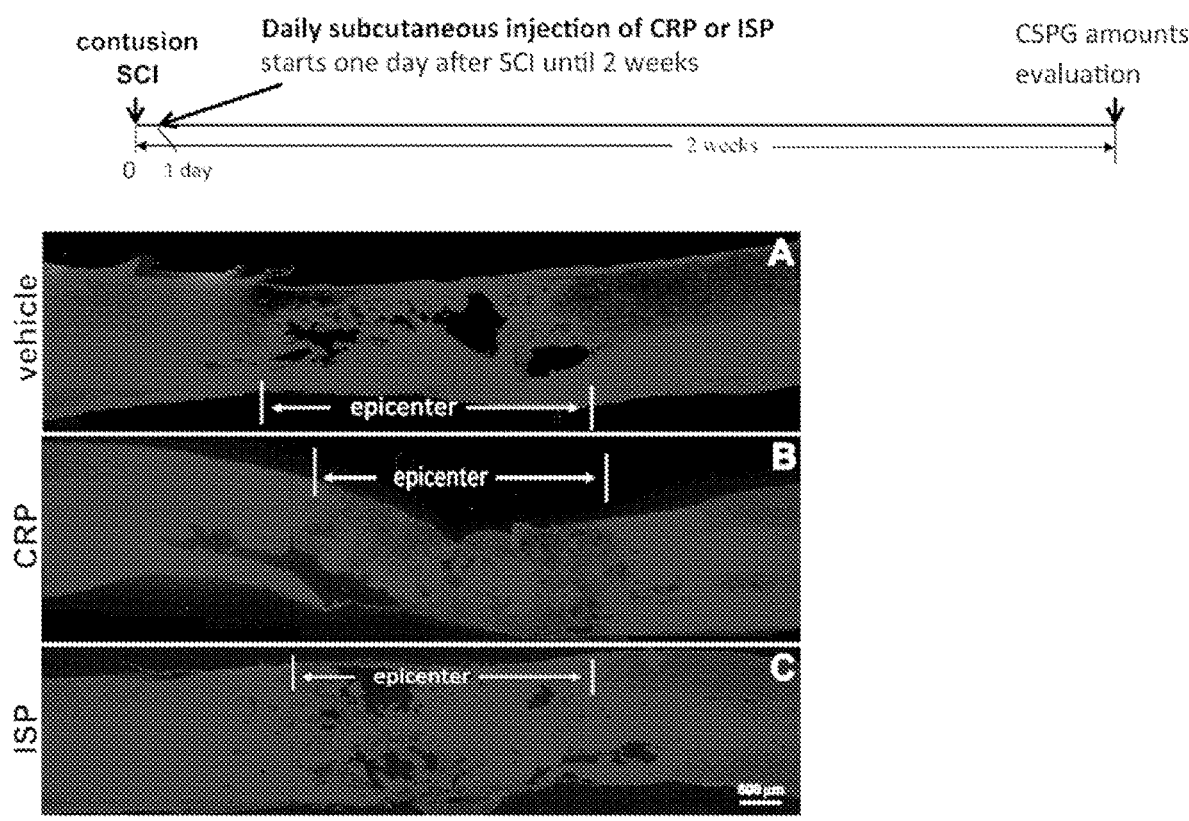
FIG. 12 shows the CRP, but not ISP, when applied one day after SCI effectively decreases CSPG in lesion epicenter and adjacent tissue two weeks after SCI. The expression of inhibitory chondroitin sulfate proteoglycan (CSPG) is upregulated surround the lesion in spinal cord two weeks after contusive SCI in the vehicle-treated animal (A). CSPG reduction peptide (CRP) treatment (B) starting one day after SCI significantly decreases SCI-induced increases in CSPG. However, intracellular sigma peptide (ISP) treatment (C) does not decrease CSPG as compared to vehicle-treated group (A).
Figure 13:
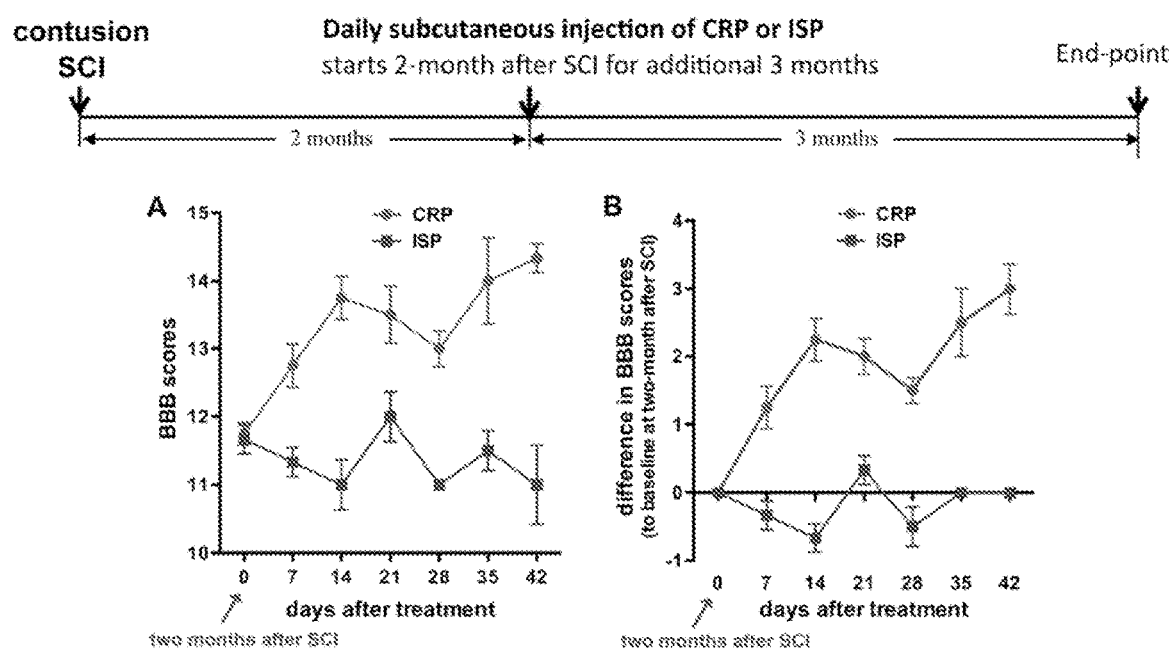
FIG. 13 shows that the CRP, but not ISP, when applied two months after SCI effectively promotes locomotion recovery. Basso, Beattie, and Bresnahan (BBB) 21-point scoring test is used as the locomotion assessment after SCI. SCI causes significant deficits on locomotion function as indicated by the significant drop of BBB scores from 21 of the normal rats. CRP treatment starting two months after contusive SCI significantly improves locomotion recovery indicated by BBB score increased from 11.75±0.164 (two months after SCI) to 14.33±0.211 (A) with average increases in BBB scores by 3.0±0.365 (B) by two months plus 42 days after SCI. However, ISP treatment slightly decreases BBB scores from 11.667±0.211 (two months after SCI) to 11.00±0.577 (two months plus 42 days after SCI) (A).

The above were followed up with studies to evaluate the treatment effects of CRP in chronic SCI. The chronic SCI is not only way more challenge to be repaired but also is the clinical status of the majority of patients with SCI. Our results find that CRP subcutaneously injected even beginning two-month after SCI still significantly improves the locomotion and voiding patterns In addition, we made a comparison of CRP with recently developed peptides, intracellular sigma peptide (ISP) targeting CSPG receptor pathways. Our data showed (1) CRP but not ISP could reduce CSPG after SCI and (2) importantly, CRP but not ISP could improve functional outcomes after chronic phase of SCI. FIG. 12 shows CRP, but not ISP, effectively decreases CSPG in lesion epicenter and adjacent tissue two weeks after SCI. FIG. 13 shows that CRP, but not ISP, when applied two months after SCI effectively promoted locomotion recovery.

Because CSPGs are the major physical barriers for axonal regeneration and functional recovery after trauma in both PNS and CNS and after neurodegenerative disorders, CRP type construction could apply to many disorders other than SCI. Indeed, CRP could be applied to limb transplants. In addition, neurodegeneration-induced increases in heparin sulfate proteoglycans (HSPGs) as well as CSPGs are unbeatable barriers for current treatment of Multiple Sclerosis (MS), which indicates the therapeutic potential of CRP to treat neurodegenerative disorders such as MS and related conditions.

Example 2

This Example describes treating spinal cord injury (SCI) in a rat model using a SOCS3 reduction peptide (SRP). The SRP had the following three components:

```
N-terminal cell membrane penetrating domain:
YGRKKRRQRRR;                (SEQ ID NO: 1)

Central CSPG binding domain from PTP sigma:
VQpYSTVVHS;                 (SEQ ID NO: 54)
and C-terminal lysosome targeting domain:
KFERQKILDQRFFE.             (SEQ ID NO: 2)
```

The full SRP sequence is as follows:

```
                                       (SEQ ID NO: 90)
    N - YGRKKRRQRRR-VQpYSTVVHS-KFERQKILDQRFFE - C.
```

Figure 14:
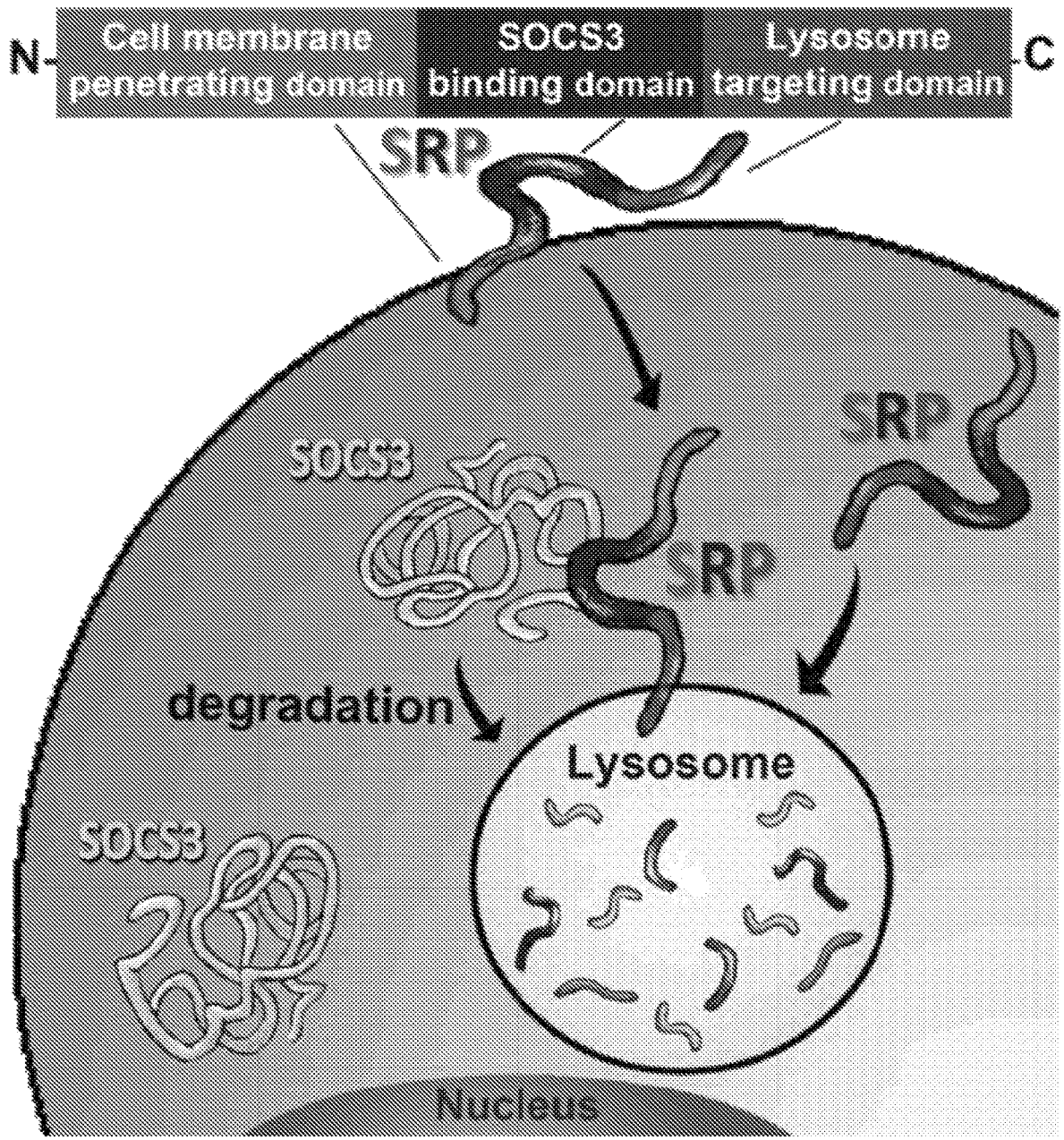
FIG. 14 shows exemplary degradation of SOCS3 using an exemplary SRP peptide. At the top of FIG. 4 is an illustration of an exemplary design of an SRP peptide, including the N-terminal cell membrane penetration domain, the central SOCS3 binding domain, and the C-terminal lysosome targeting domain that directs SRP-bound SOCS3 to lysosomes for degradation.

The designed SRP (SEQ ID NO:90) includes an N-terminal cell membrane-penetrating domain (SEQ ID NO:1), a central SOCS3 binding domain (SEQ ID NO:54), and a C-terminal lysosome targeting domain (SEQ ID NO:2) for directing the SRP-SOCS3 complex to lysosomes for degradation. FIG. 14 shows a schematic of the exemplary SRP employed in this Example.

In this Example, the SRP has been applied in a preclinical rat model to test the efficacy of the treatment of spinal cord injury (SCI) in a manner similar to Example 1 above for CRP. The results are as follows.

Figure 15:
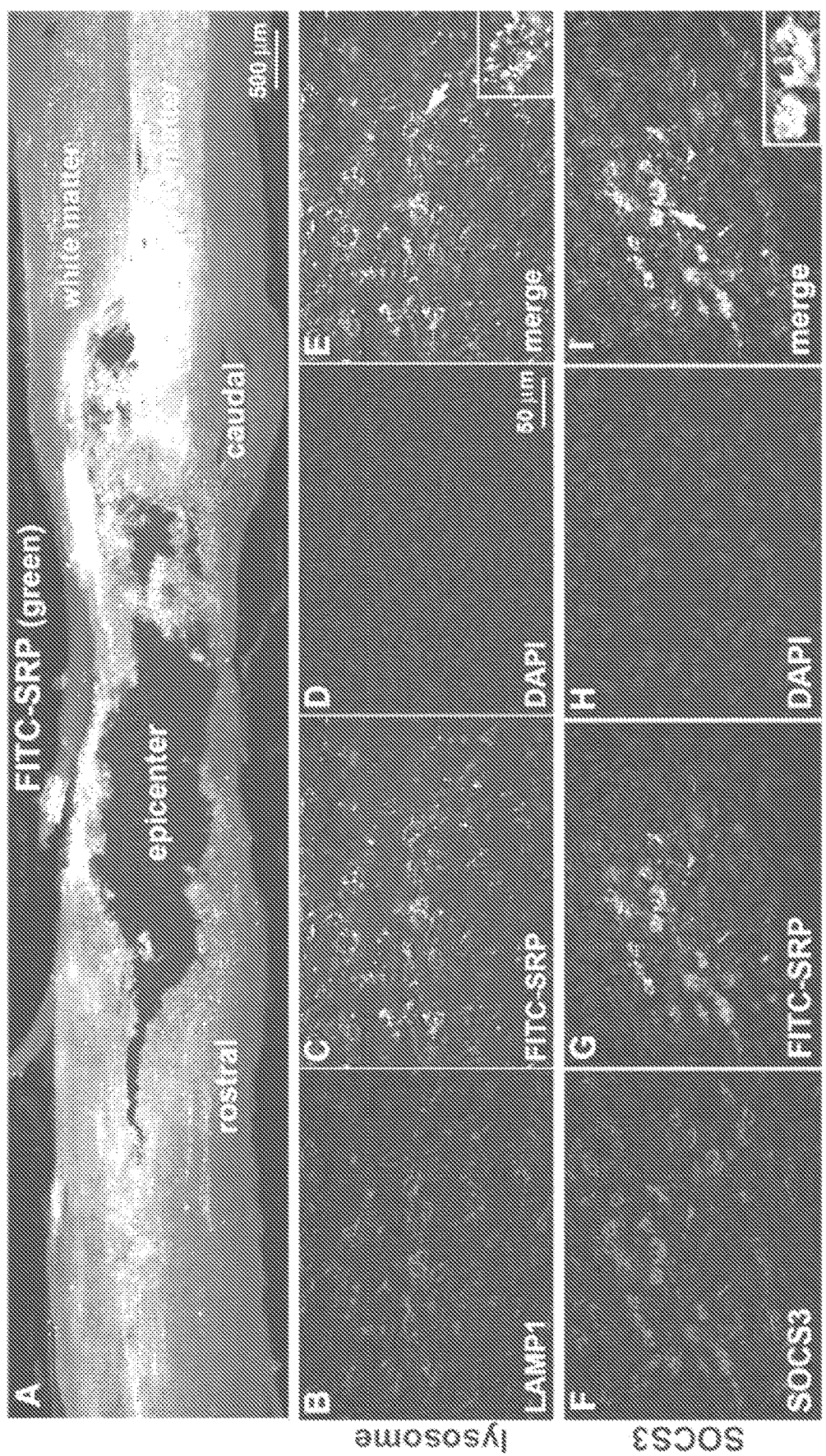
FIG. 15 shows the distribution of FITC-labeled SRP in the spinal cord and in lysosomes of target cells 8 days after contusive SCI. A single subcutaneous injection of FITC-SRP was administered 8 days after contusive SCI. Spinal cords were harvested 3 hours after injection. A, Representative image demonstrating FITC-labeled SRP (green) distributed surrounding the injury epicenter and in both gray matter and white matter. B-E, Representative 3D deconvolution images of co-localization (arrow, E) of FITC-SRP (C) with the lysosomal marker LAMP1 (B) in the spinal cord surrounding the injury epicenter. F-I, Singly injected FITC-SRP (G) co-localized (I) with SCI increased SOCS3 (F) in the areas surrounding the lesion epicenter at 8 days post SCI. The boxed area shows higher magnification of co-localization observed in the area indicated by the arrow.

FIG. 15 shows the distribution of FITC-labeled SRP (FITC-SRP) in the spinal cord and in lysosomes of target cells 8 days after contusive SCI. A single subcutaneous injection of FITC-SRP was administered 8 days after contusive SCI. Spinal cords were harvested 3 hours after injection. A, Representative image demonstrating FITC-labeled SRP (green) distributed surrounding the injury epicenter and in both gray matter and white matter. B-E, Representative 3D deconvolution images of co-localization (arrow, E) of FITC-SRP (C) with the lysosomal marker LAMP1 (B) in the spinal cord surrounding the injury epicenter. F-I, Singly injected FITC-SRP (G) co-localized (I) with SCI increased SOCS3 (F) in the areas surrounding the lesion epicenter at 8 days post SCI. The boxed area shows higher magnification of co-localization observed in the area indicated by the arrow.

Figure 16:
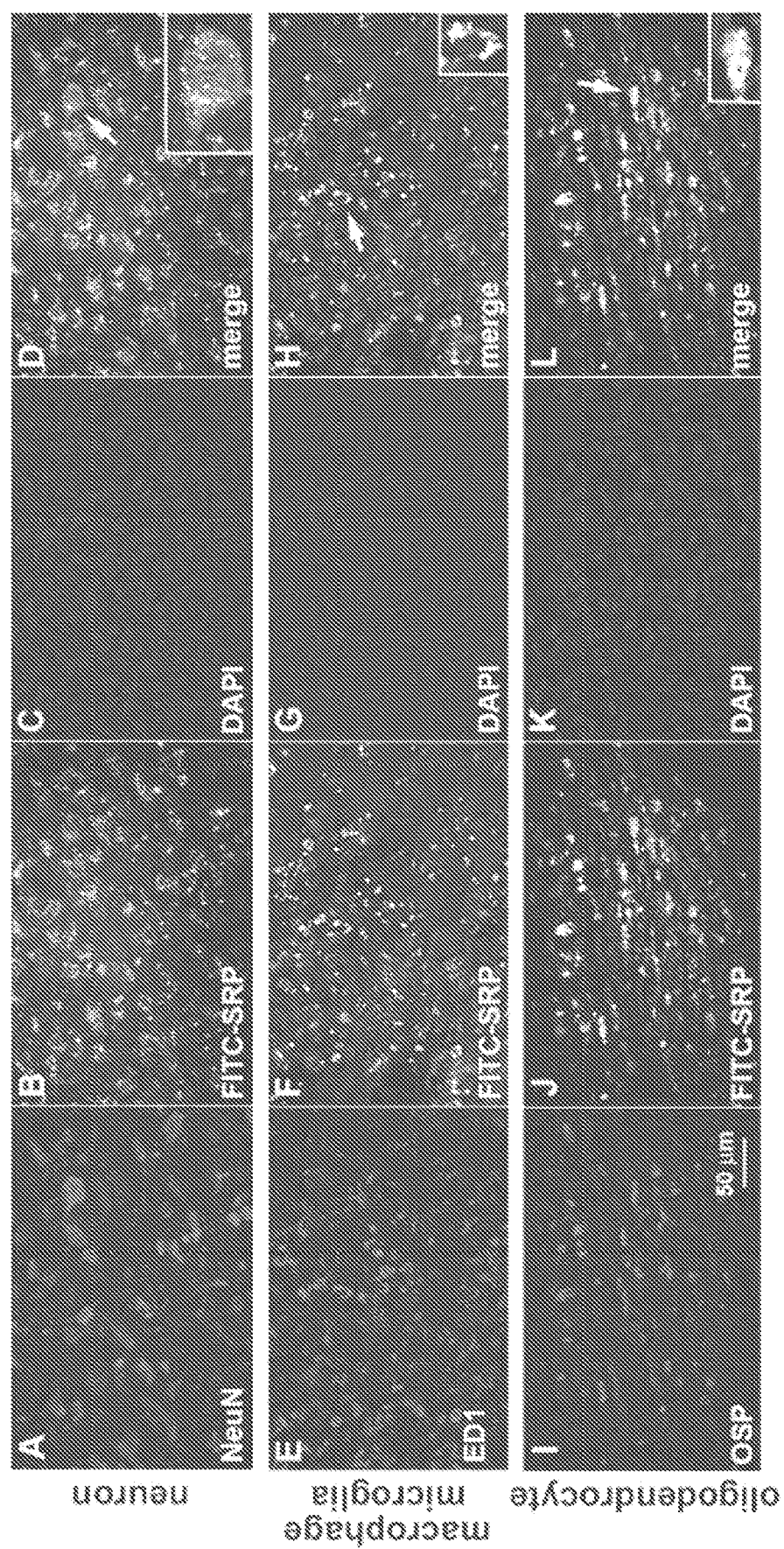
FIG. 16 shows that FITC-SRP was identified in neurons, microglia/macrophages, and oligodendrocytes. Representative 3D deconvolution images show the co-localization of FITC-SRP and neurons (NeuN+; A-D), or microglia/macrophages (ED1+; E-H), or oligodendrocytes (OSP+; I-L). The boxed area shows higher magnification of co-localized cells (arrow).

FIG. 16 shows that FITC-SRP was identified in neurons, microglia/macrophages, and oligodendrocytes. Representative 3D deconvolution images show the co-localization of FITC-SRP and neurons (NeuN+; A-D), or microglia/macrophages (ED1+; E-H), or oligodendrocytes (OSP+; I-L). The boxed area shows higher magnification of co-localized cells (arrow).

Figure 17:
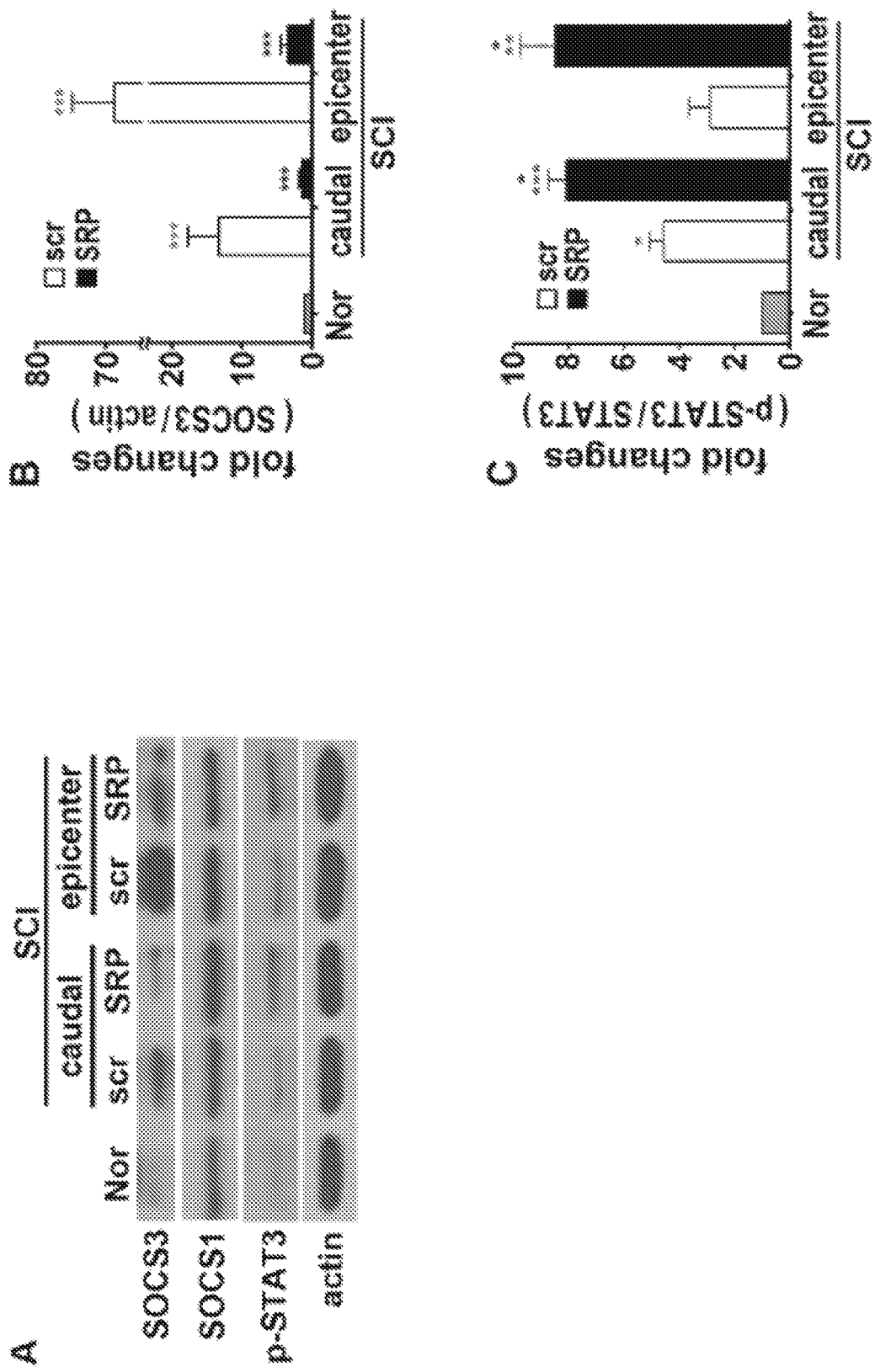
FIG. 17 shows SRP significantly reduced SOCS3 levels in the spinal cord after SCI. SOCS3 protein expression in the spinal cord of the scrambled peptide group (scr) was significantly increased 7 days after SCI at the epicenter and in areas caudal to the injured site compared to normal rats (Nor). The SCI-upregulated SOCS3 was significantly reduced by SRP treatment (SRP) beginning one day after SCI (once per day). Additionally, significant activation of STAT3, as indicated by phospho-STAT3 Tyr705 (p-STAT3) expression, was observed in SRP-treated SCI animals. SOCS1 and actin were not significantly altered by SRP treatment (A). Graphs represent mean±SEM of five samples per group for the ratios of SOCS3 to actin (B) and p-STAT3 to STAT3 (C).

FIG. 17 shows SRP significantly reduced SOCS3 levels in the spinal cord after SCI. SOCS3 protein expression in the spinal cord of the scrambled peptide group (scr) was significantly increased 7 days after SCI at the epicenter and in areas caudal to the injured site compared to normal rats (Nor). The SCI-upregulated SOCS3 was significantly reduced by SRP treatment (SRP) beginning one day after SCI (once per day). Additionally, significant activation of STAT3, as indicated by phospho-STAT3 Tyr705 (p-STAT3) expression, was observed in SRP-treated SCI animals. SOCS1 and actin were not significantly altered by SRP treatment (A). Graphs represent mean±SEM of five samples per group for the ratios of SOCS3 to actin (B) and p-STAT3 to STAT3 (C). +$p<0.05$, ++$p<0.01$, and +++$p<0.001$ compared to normal animals, and *$p<0.05$ and ***$p<0.001$ compared to scrambled peptide animals (two way ANOVA with Bonferroni multiple analyses).

Figure 18:
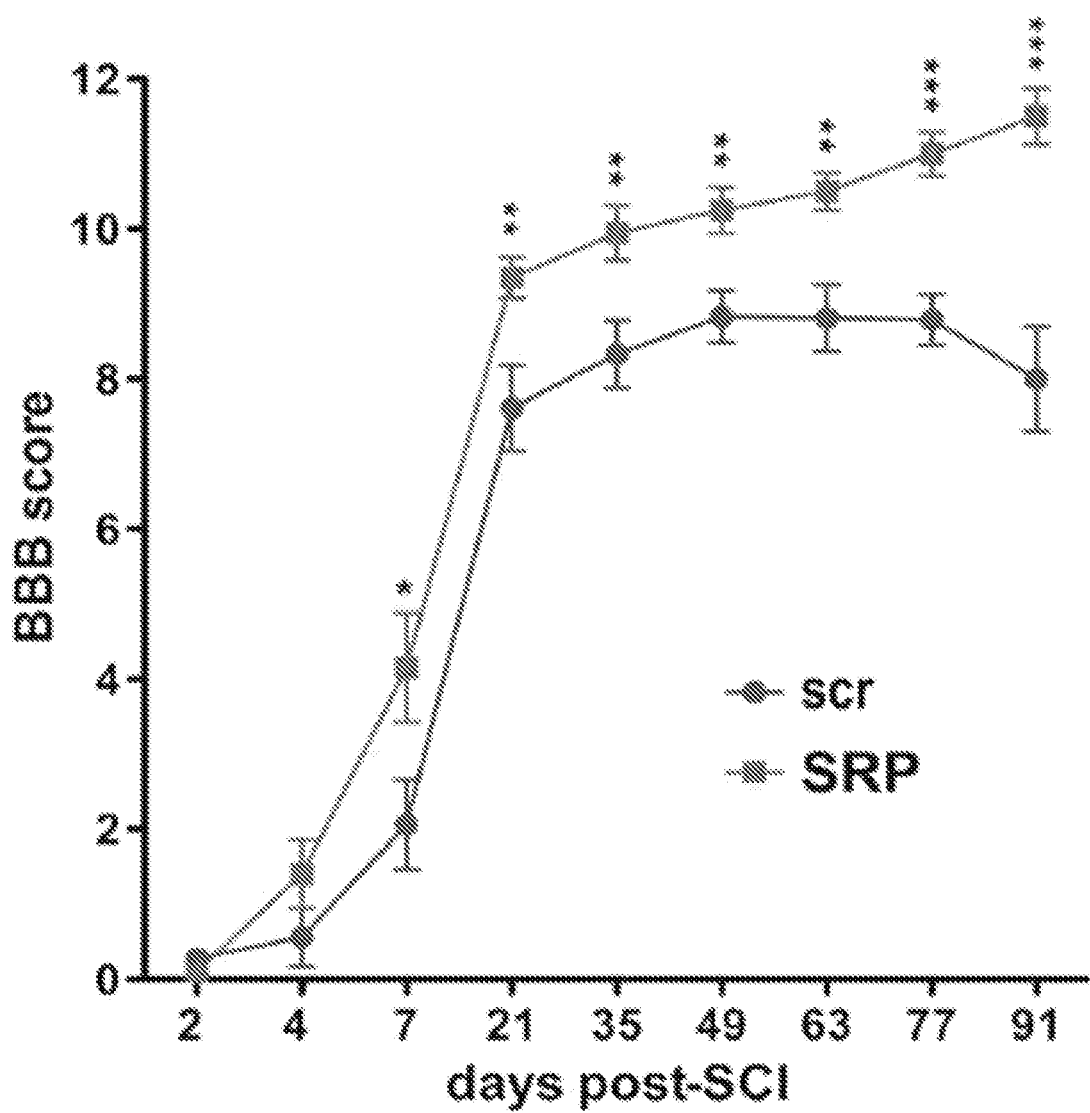
FIG. 18 shows improvement of hind limb motor function with SRP treatment following T8 contusive SCI. Animals were subcutaneously injected with SRP daily for one month beginning one day after SCI and assessed by the BBB open field locomotion test to evaluate hind limb motor function at the designated time points. SRP-treated animals showed significant improvement in hind limb locomotion as compared to scrambled peptide (scr)-treated animals over the entire observation period.

FIG. 18 shows improvement of hindlimb motor function with SRP treatment following T8 contusive SCI. Animals were subcutaneously injected with SRP daily for one month beginning one day after SCI and assessed by the BBB open field locomotion test to evaluate hind limb motor function at the designated time points. SRP-treated animals showed significant improvement in hind limb locomotion as compared to scrambled peptide (scr)-treated animals over the entire observation period. *$p<0.05$, $p<0.01$, and *$p<0.001$; two-way ANOVA. Values represent mean±SEM.

Figure 19:
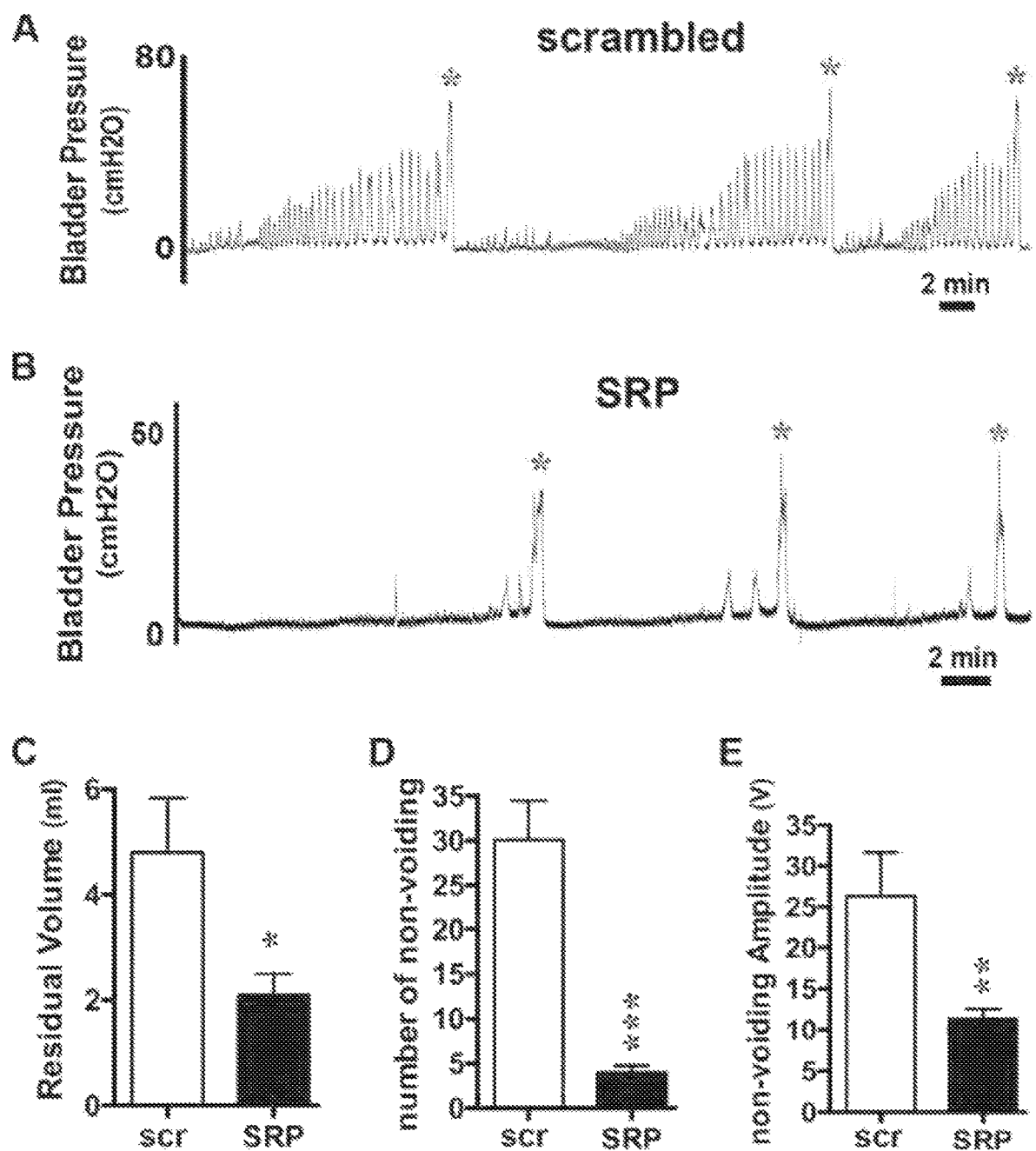
FIG. 19 shows SRP treatment improved bladder function after T8 contusive SCI. Animals were treated daily with SRP for one month, beginning one day after SCI. Urodynamic analyses were conducted 3 months post-SCI. A representative cystometrograms (CMG) of three cycles of micturition events (red * indicates where micturition occurred) shows hyperactive bladder activity before reaching the voiding point in scrambled peptide-treated animals (A). SRP treatment (SRP) significantly reduced bladder hyperactivity (B). Statistical analysis revealed that SRP significantly reduced (C) residual volume, (D) the number of non-voiding contractions, and (E) the non-voiding contraction amplitude when compared to the scrambled peptide group (scr).
Figure 19:
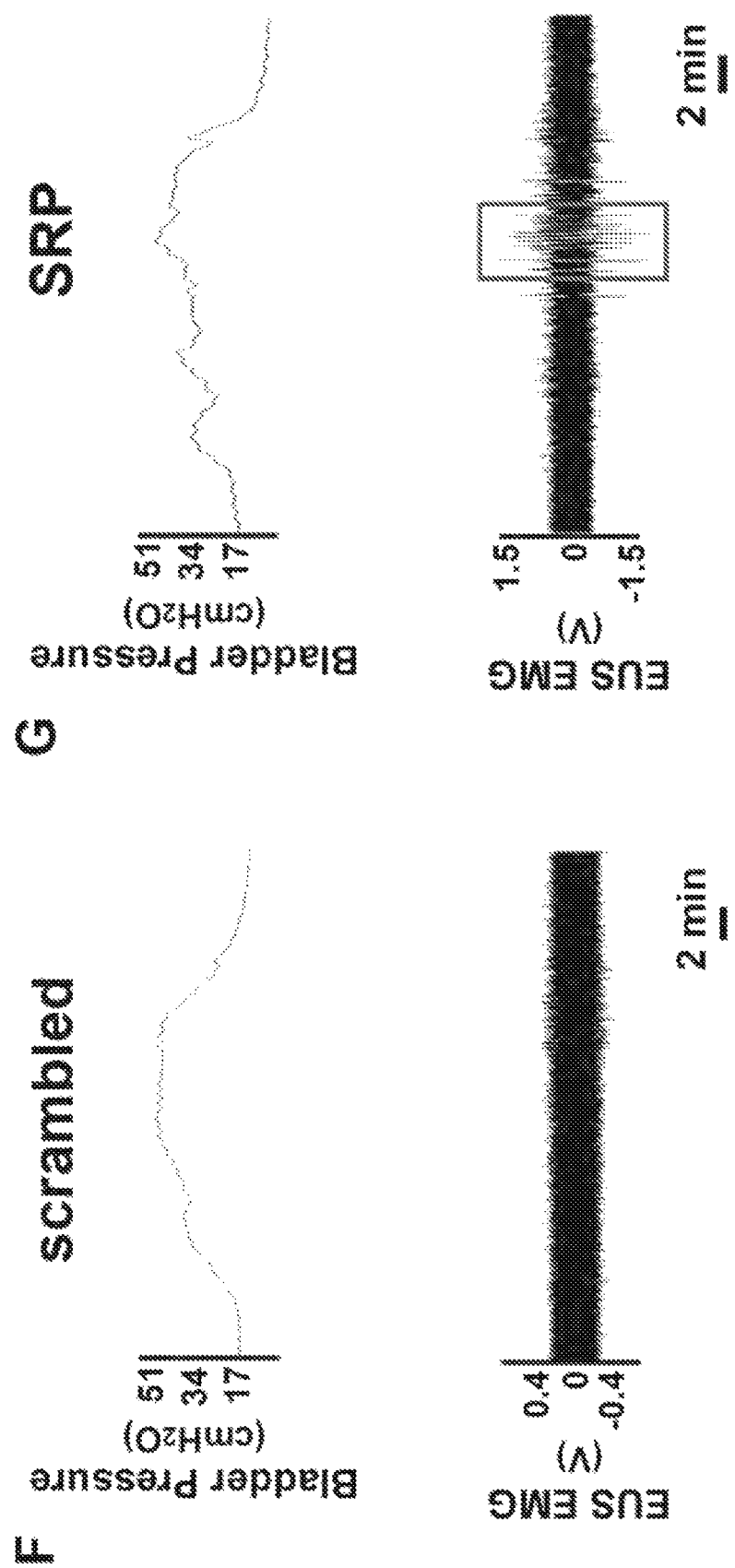

FIG. 19 shows SRP treatment improved bladder function after T8 contusive SCI. Animals were treated daily with SRP for one month, beginning one day after SCI. Urodynamic analyses were conducted 3 months post-SCI. A representative cystometrograms (CMG) of three cycles of micturition events (red * indicates where micturition occurred) shows hyperactive bladder activity before reaching the voiding point in scrambled peptide-treated animals (A). SRP treatment (SRP) significantly reduced bladder hyperactivity (B). Statistical analysis revealed that SRP significantly reduced (C) residual volume, (D) the number of non-voiding contractions, and (E) the non-voiding contraction amplitude when compared to the scrambled peptide group (scr). *$p<0.05$, $p<0.01$ and *$p<0.001$ (two-tailed t test, n=8 per group). FIG. 19 (F and G) also shows SRP treatment improved bursting activities of external urethral sphincter (EUS) recorded by electromyogram (EMG) after T8 contusive SCI. EUS EMG recording were conducted 3 months post-SCI. The EUS EMG during the void period showed improvement in bursting activity indicated by red rectangle following SRP (G) when compared to the scrambled peptide (scrambled) group (F).

Figure 20:
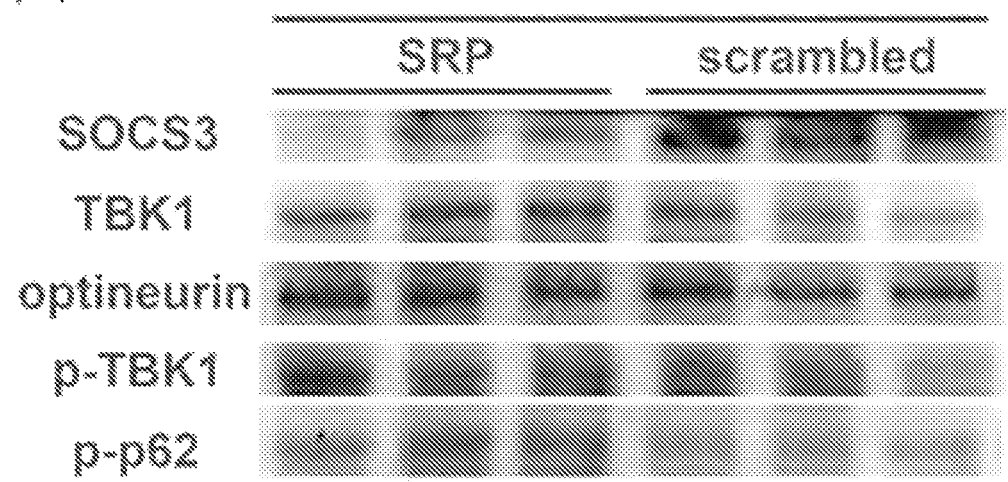
FIG. 20 shows that SRP significantly increased TBK1 and mitophagy adaptors in the spinal cord after SCI. SCI-upregulated SOCS3 was significantly reduced by SRP treatment (SRP) beginning one day after SCI (once per day) compared to the scrambled peptide group (scr). The protein levels of TBK1 and optineurin were significantly increased with SRP treatment. Additionally, significant activation of TBK1 and p62, as indicated by phospho-TBK1 Ser172 (p-TBK1) and phosphor-p62 Ser403 (p-p62) expression, was observed in SRP-treated SCI animals. (A). Graphs represented mean±SEM of six samples per group for the % to GAPDH (B).
Figure 20:
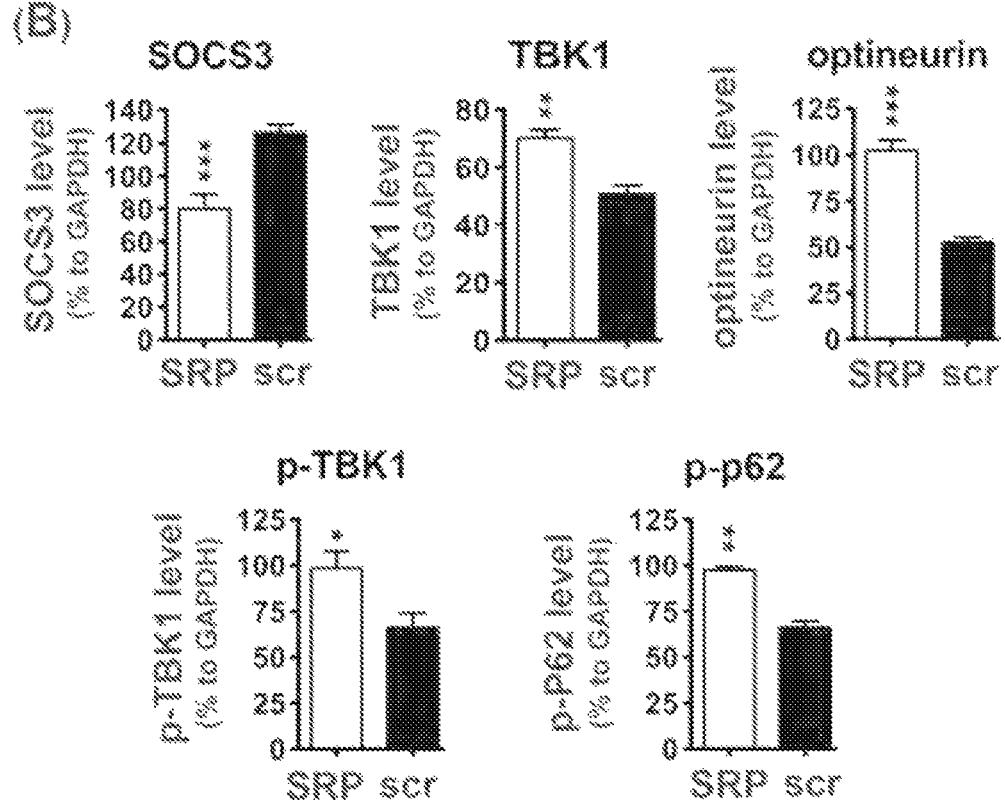

FIG. 20 shows that SRP significantly increased TBK1 and mitophagy adaptors in the spinal cord after SCI. SCI-upregulated SOCS3 was significantly reduced by SRP treatment (SRP) beginning one day after SCI (once per day) compared to the scrambled peptide group (scr). The protein levels of TBK1 and optineurin were significantly increased with SRP treatment. Additionally, significant activation of TBK1 and p62, as indicated by phospho-TBK1 Ser172 (p-TBK1) and phosphor-p62 Ser403 (p-p62) expression, was observed in SRP-treated SCI animals. (A). Graphs represented mean±SEM of six samples per group for the % to GAPDH (B). *$p<0.05$, $p<0.01$ and *$p<0.001$ compared to scrambled peptide animals (two-tailed t test, n=3 per group).

Figure 21:
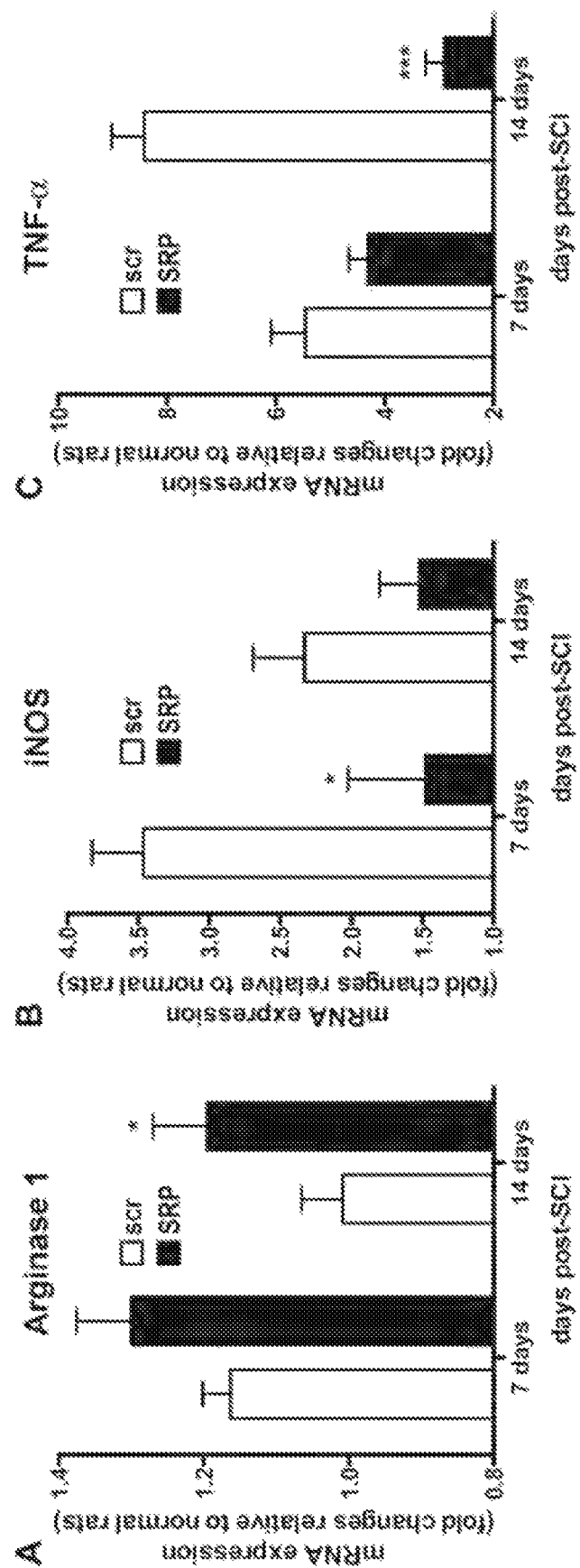
FIG. 21 shows qRT-PCR analyses of markers for pro- vs. anti-inflammatory macrophages in spinal cord segments caudal to the injury site. Rats were treated once per day beginning one day after SCI with SRP or scrambled peptide (scr) and mRNA was then harvested and analyzed by qRT-PCR. As shown, SRP treatment increased arginase 1 (A), but decreased iNOS (B) expression, at both 7 and 14 days post-SCI. C. Notably, SRP decreased TNF-α expression at 7 days post-SCI, which was even more pronounced at 14 days post-SCI.

FIG. 21 shows qRT-PCR analyses of markers for pro- vs. anti-inflammatory macrophages in spinal cord segments caudal to the injury site. Rats were treated once per day beginning one day after SCI with SRP or scrambled peptide (scr) and mRNA was then harvested and analyzed by qRT-PCR. As shown, SRP treatment increased arginase 1 (A), but decreased iNOS (B) expression, at both 7 and 14 days post-SCI. C. Notably, SRP decreased TNF-α expression at 7 days post-SCI, which was even more pronounced at 14 days post-SCI. *$p<0.05$ and ***$p<0.001$ compared to scrambled peptide-treated animals, two-way ANOVA with Bonferroni multiple analyses, mean±SEM, n=3 per group.

Figure 22:
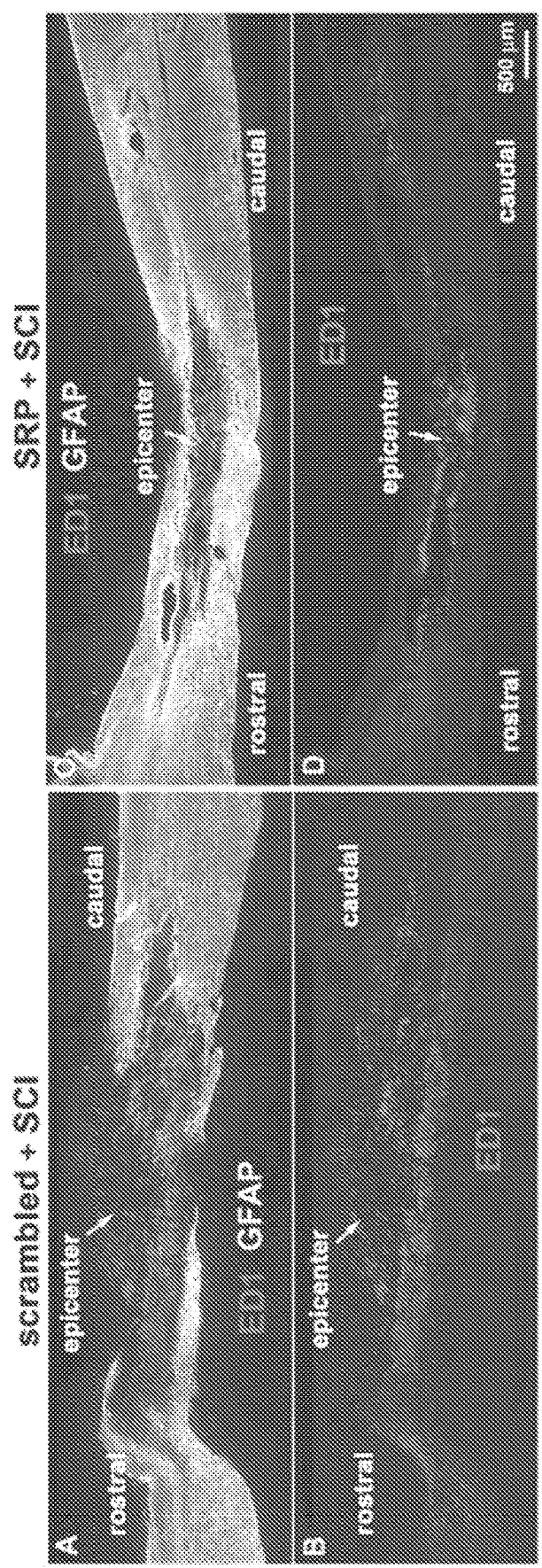
FIG. 22 shows SRP treatment robustly decreased SCI-increased ED1+ macrophages/microglia. SRP treatment beginning one day after SCI was administered for 30 consecutive days and then spinal cords were harvested three months post-SCI for double immunolabeling of ED1 and GFAP. As shown, SRP treatment blocked SCI-induced upregulation of ED1+ macrophages (C, D), but preserved more GFAP+ tissues (A, B) in the areas surrounding the lesion epicenter when compared to scrambled peptide (scrambled)-treated groups.

FIG. 22 shows SRP treatment robustly decreased SCI-increased ED1+ macrophages/microglia. SRP treatment beginning one day after SCI was administered for 30 consecutive days and then spinal cords were harvested three months post-SCI for double immunolabeling of ED1 and GFAP. As shown, SRP treatment blocked SCI-induced upregulation of ED1+ macrophages (C, D), but preserved more GFAP+ tissues (A, B) in the areas surrounding the lesion epicenter when compared to scrambled peptide (scrambled)-treated groups.

Figure 23:
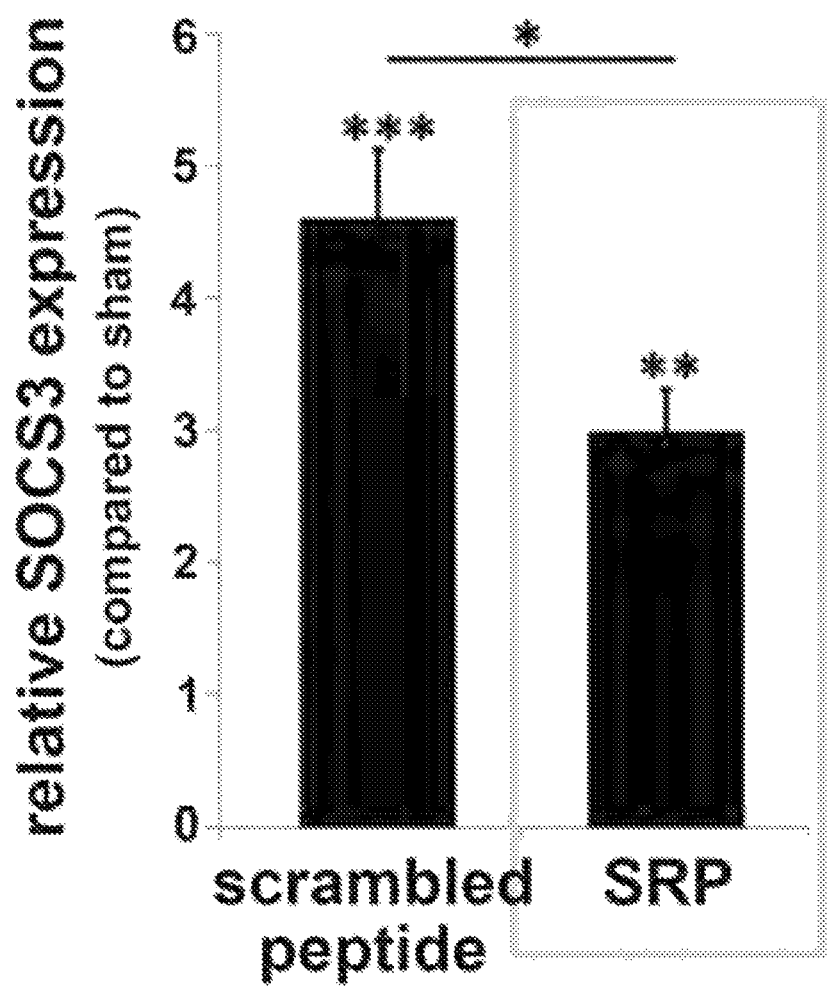
FIG. 23 shows SRP significantly reduced SOCS3 levels in the sciatic nerve after sciatic nerve transection. The sciatic nerve transection-upregulated SOCS3 was significantly reduced by SRP treatment (SRP) beginning immediately after sciatic nerve transection for 4 consecutive days (once per day).

FIG. 23 shows SRP significantly reduced SOCS3 levels in the sciatic nerve after sciatic nerve transection. The sciatic nerve transection-upregulated SOCS3 was significantly reduced by SRP treatment (SRP) beginning immediately after sciatic nerve transection for 4 consecutive days (once per day). $p<0.01$ and *$p<0.001$ compared to normal animals, and *$p<0.05$ compared to scrambled peptide treated animals (two-tailed t test, n=4 per group).

Example 3

This Example describes additional in vitro and in vivo work with the CSPG reduction peptide (CRP) described in Example 1.

Figure 24:
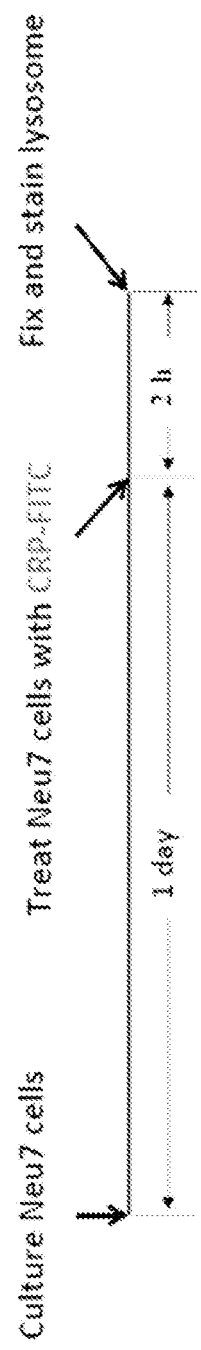
FIG. 24 shows that applied CRP is found in the lysosome of Neu7 astrocytes and provides the results of an in vitro assays that demonstrates the concept of lysosmoal target domain in CRP. Such an in vitro assay was used to demonstrate the co-localization of FITC-CRP and lysosomal marker (LAMP1). Representative images indicate that FITC-CRP is brought to lysosomes (LAMP1+) for degradation after entering Neu7 cells (arrow).
Figure 24:

FIG. 24 shows that applied CRP is found in the lysosome of Neu7 astrocytes and provides the results of an in vitro assays that demonstrates the concept of lysosmoal target domain in CRP. Such an in vitro assay was used to demonstrate the co-localization of FITC-CRP and lysosomal marker (LAMP1). Representative images indicate that FITC-CRP is brought to lysosomes (LAMP1+) for degradation after entering Neu7 cells (arrow).

Figure 25:
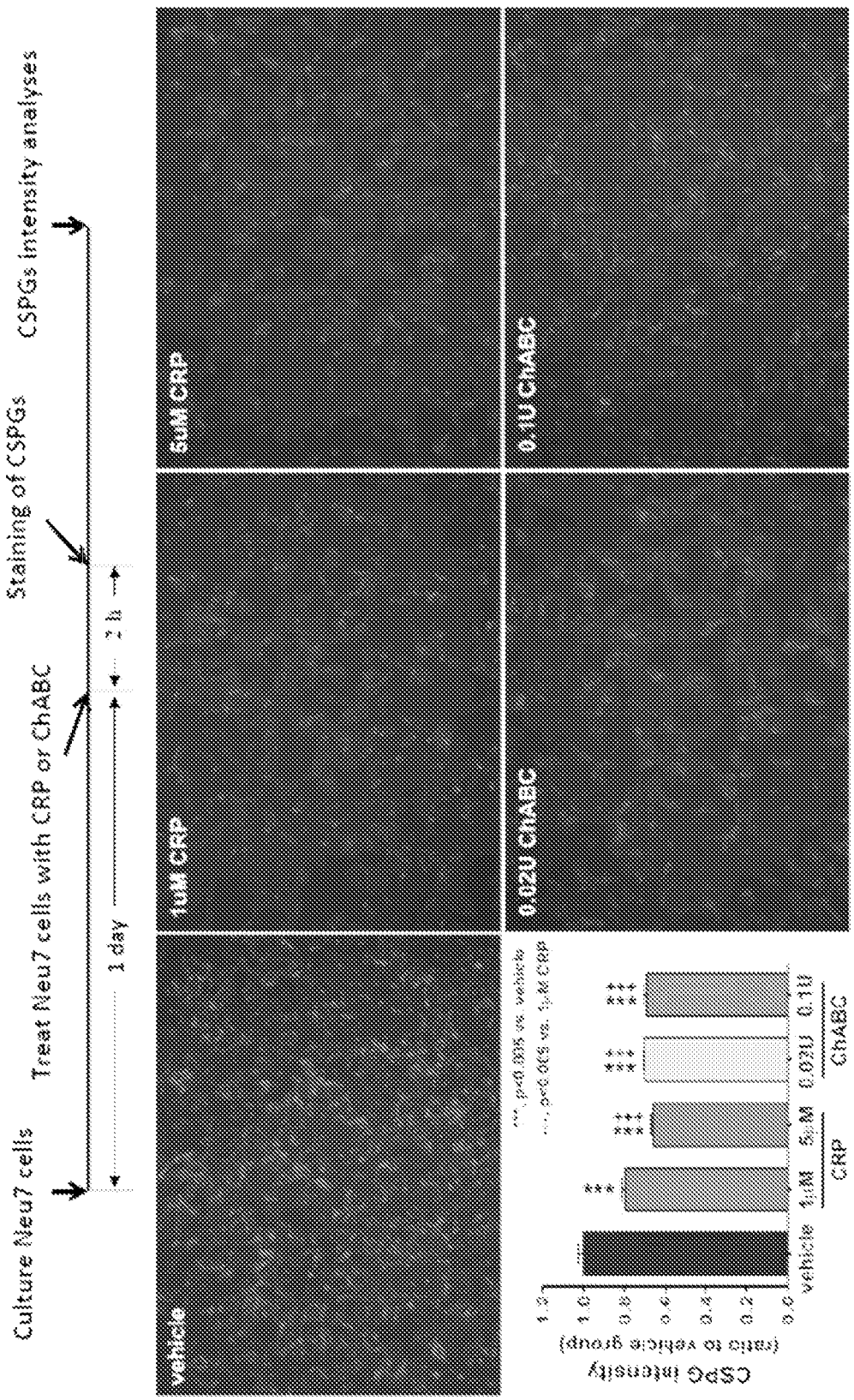
FIG. 25 shows that CRP significantly decreases Neu7-produced CSPGs. In particular.

FIG. 25 shows that CRP significantly decreases Neu7-produced CSPGs. In particular, FIG. 25 shows that CRP significantly reduces CSPG produced by Neu7 cells to a comparable level what ChABC does. Note there is also a dosage response by CRP application.

Figure 26:
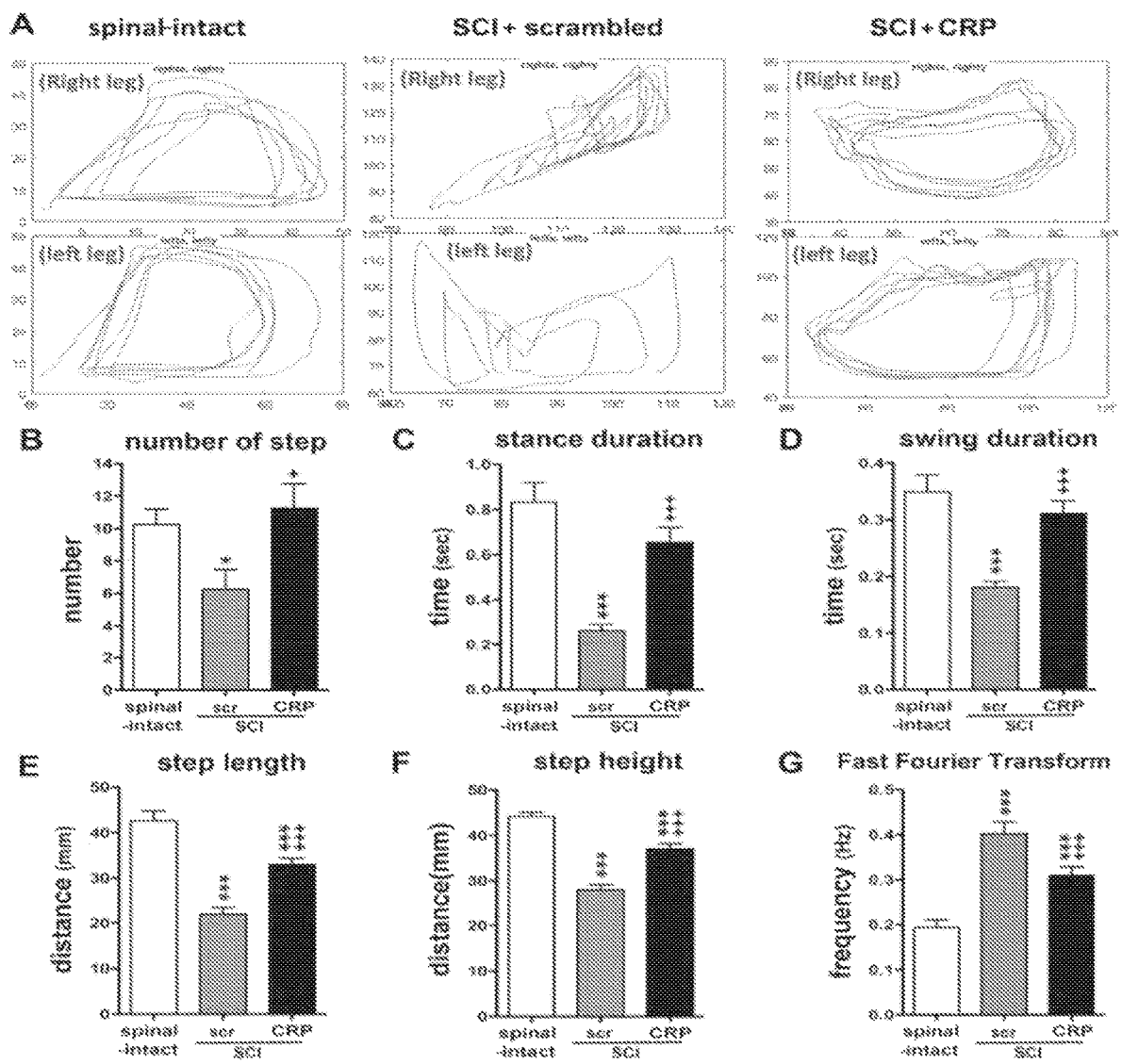
FIG. 26 shows that CRP treatment improves gait patterns after SCI in rats. In particular

FIG. 26 shows that CRP treatment improves gait patterns after SCI in rats. In particular FIG. 26 shows Kinematics assessment in SCI rats. (A) Representative total of hindlimb movement trajectories for spinal-intact, SCI+scrambled peptide (scr) and SCI+CRP groups at 3 months post-SCI. (B-G) CRP treatment significantly improved several parameters of gait pattern with trajectories more consistent to what the spinal-intact animals did, when compared to scr treatment. *, $P<0.05$; ***, $P<0.001$ when compared to the spinal-intact group; +, $P<0.05$; +++, $P<0.001$ when compared to scr group. N=6 to 8 per group.

Figure 27:
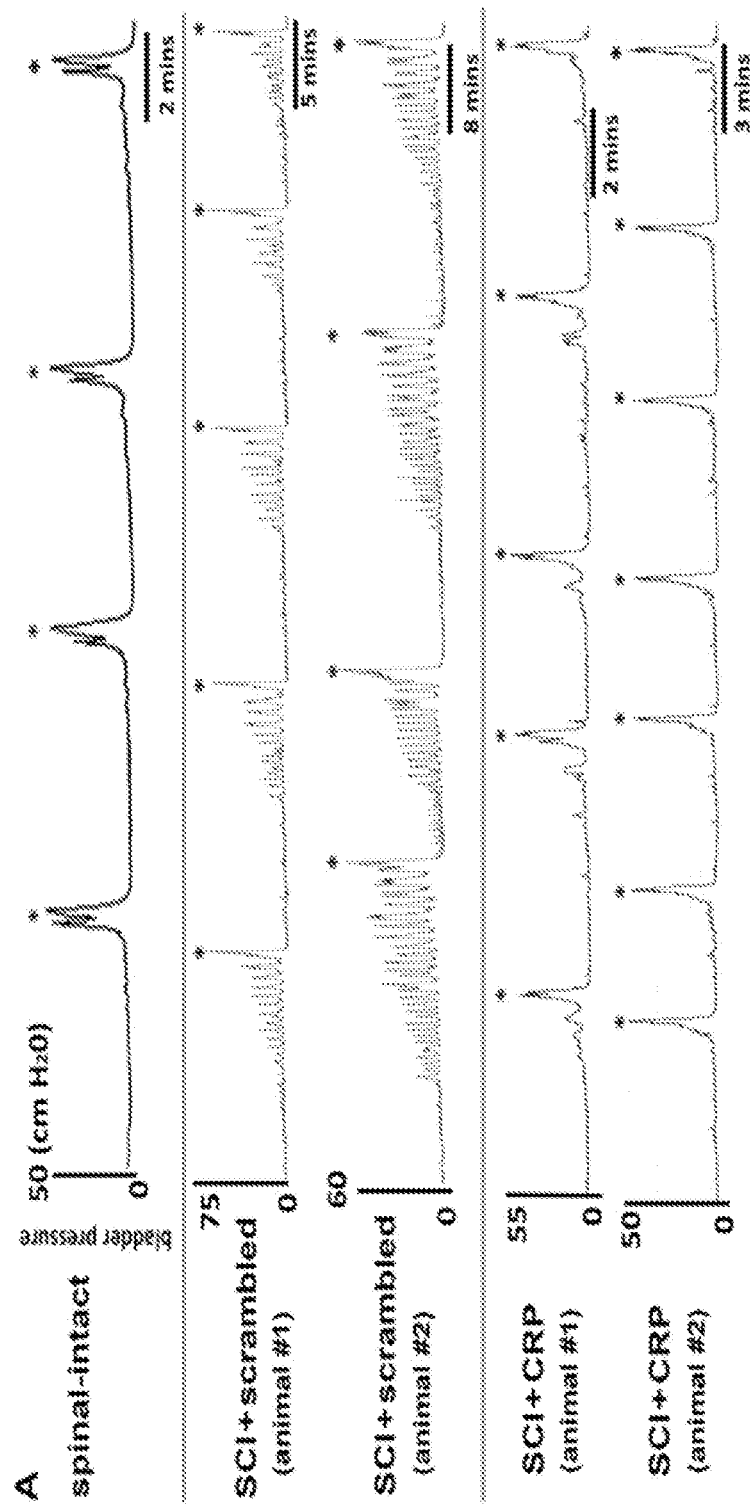
FIG. 27 shows that CRP treatment improves bladder function after SCI. (A) Representative cystometrograms (CMG) with micturition (voiding) events (indicated by asterisk) for spinal-intact, SCI+scrambled peptide (scr) and SCI+CRP groups at 3 months post-SCI. (B~H) CRP treatment reduces hyperactive bladder and improve CMG parameters including lower voiding pressure and smaller bladder capacity when compared to scr application after T8 SCI.
Figure 27:
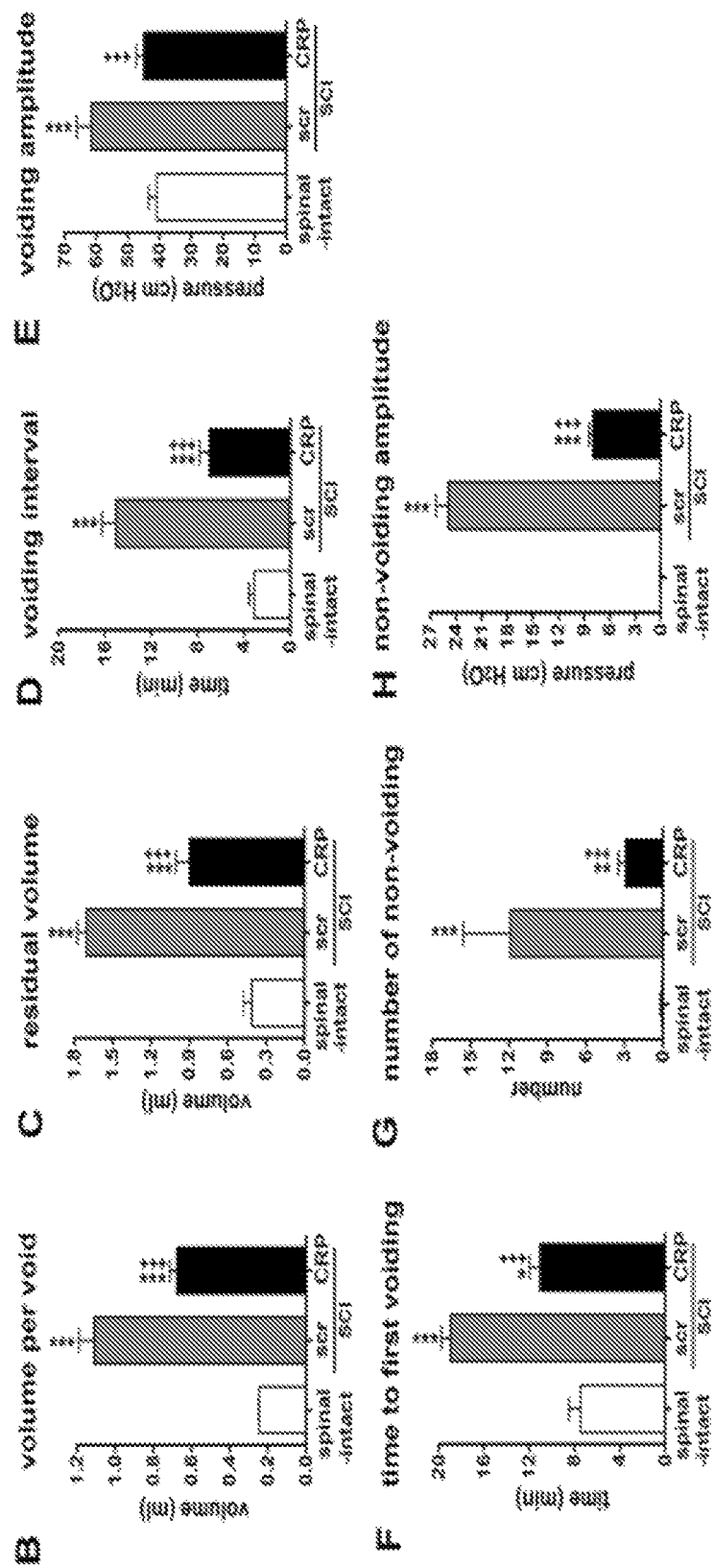

FIG. 27 shows that CRP treatment improves bladder function after SCI. (A) Representative cystometrograms (CMG) with micturition (voiding) events (indicated by asterisk) for spinal-intact, SCI+scrambled peptide (scr) and SCI+CRP groups at 3 months post-SCI. (B~H) CRP treatment reduces hyperactive bladder and improve CMG parameters including lower voiding pressure and smaller bladder capacity when compared to scr application after T8 SCI. *, P<0.05; , P<0.01; *, P<0.001 when compared to the spinal-intact group; +++, P<0.001 when compared to the scr group. N=6 to 8 per group.

Figure 28:
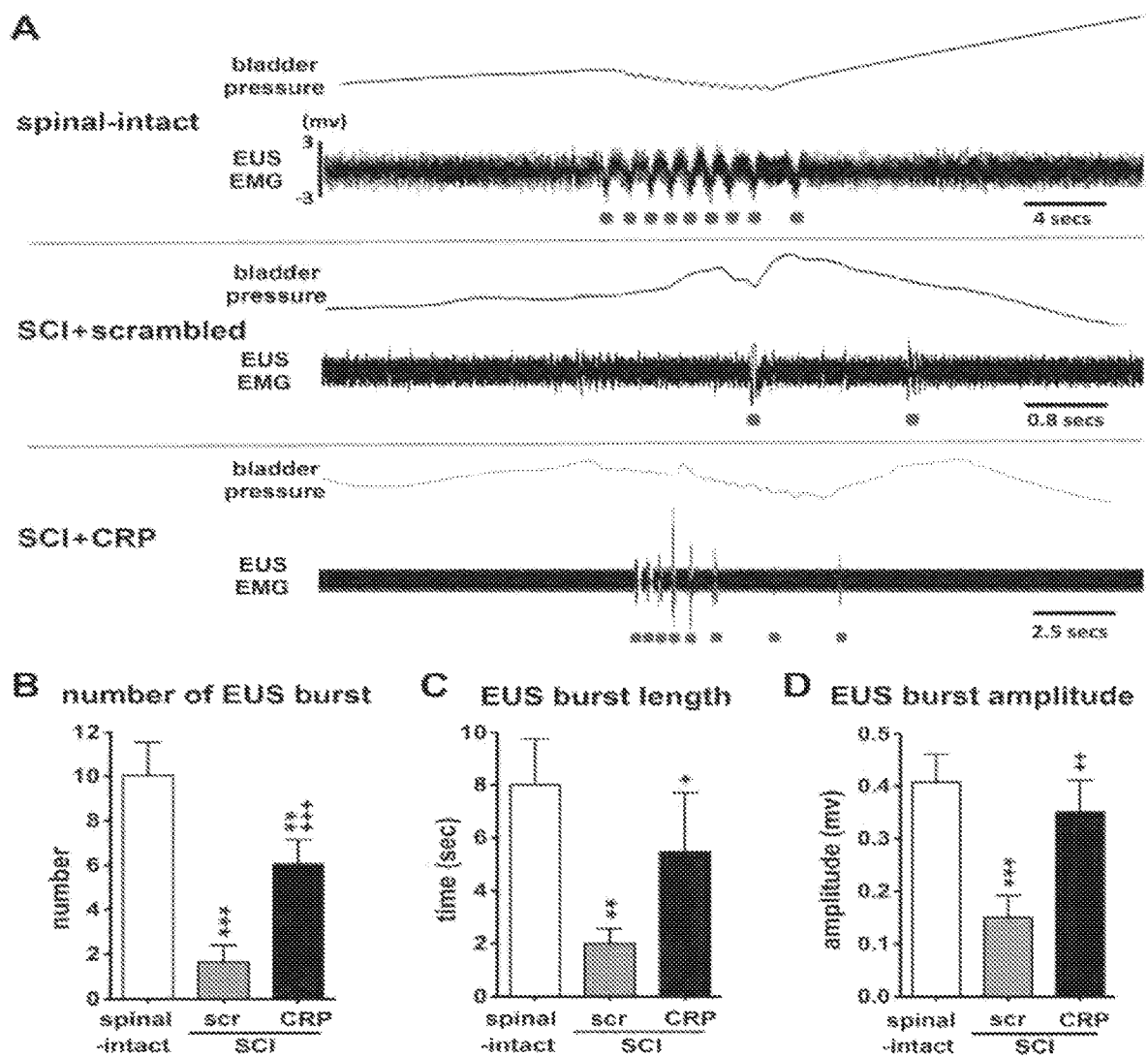
FIG. 28 shows that CRP treatment improves EUS EMG activity during the void after SCI (more bursting number and larger bursting amplitude). (A) Representative cystometrograms (CMG) with external urethral sphincter (EUS) electromyogram (EMG) recordings at micturition events for spinal-intact, SCI+scrambled peptide (scr) and SCI+CRP groups at 3 months post-SCI. (B~D) CRP treatment improves EUS bursting activity when compared to scr application after T8 SCI. The red dot indicates bursting activity.

FIG. 28 shows that CRP treatment improves EUS EMG activity during the void after SCI (more bursting number and larger bursting amplitude). (A) Representative cystometrograms (CMG) with external urethral sphincter (EUS) electromyogram (EMG) recordings at micturition events for spinal-intact, SCI+scrambled peptide (scr) and SCI+CRP groups at 3 months post-SCI. (B~D) CRP treatment improves EUS bursting activity when compared to scr application after T8 SCI. The red dot indicates bursting activity. , P<0.01; *, P<0.001 when compared to the spinal-intact group; +, P<0.05, ++, P<0.01; +++, P<0.001 when compared to the scr group. N=6 to 8 per group.

Figure 29:
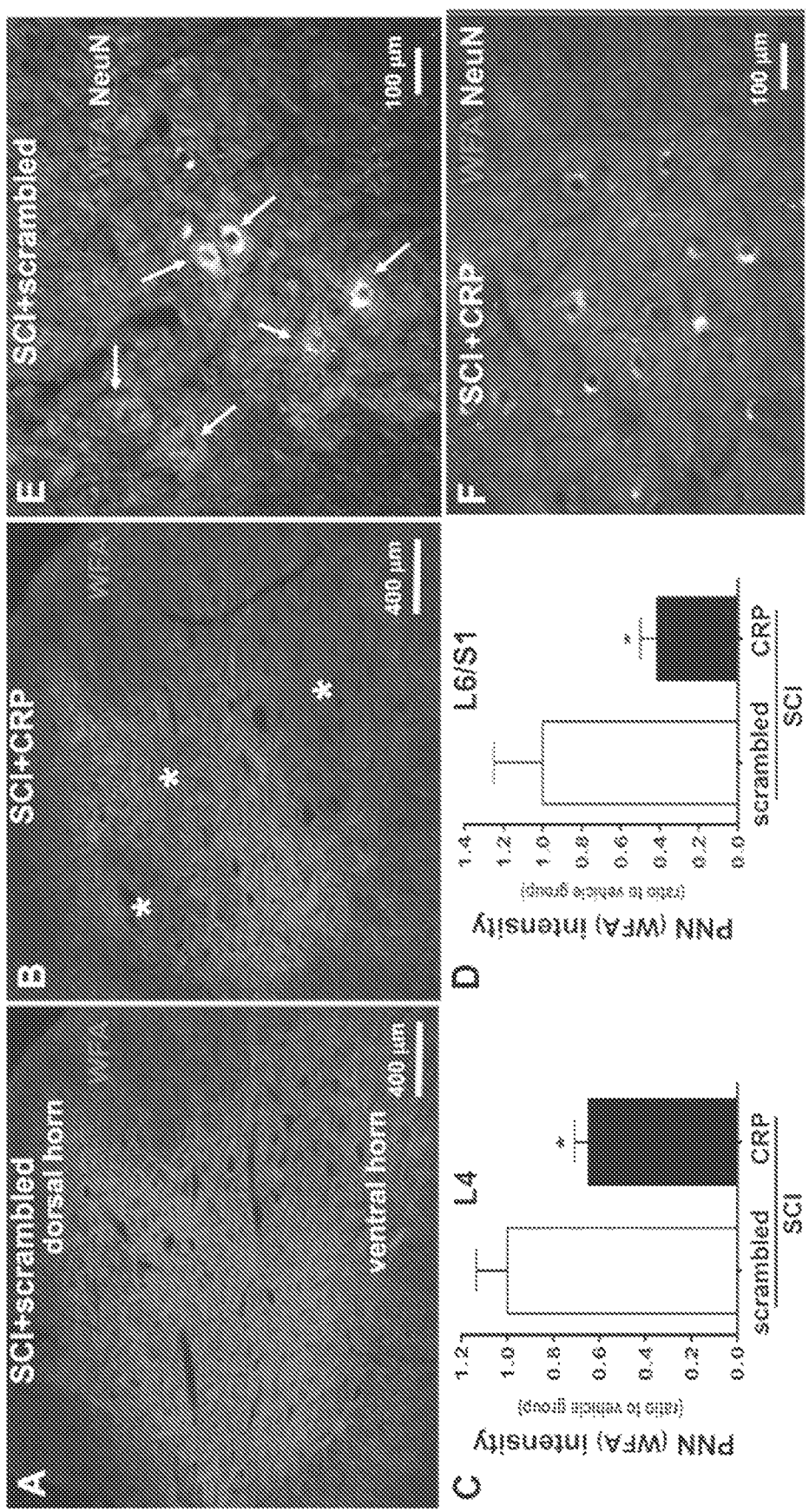
FIG. 29 shows that CRP treatment reduced PNN in lumbosacral spinal cord after T8 SCI, and particularly shows the anatomical assessments of perineuronal nets (PNN) in SCI rats. (A, B) Representative L4 spinal cord transverse images show CRP treatment reduces overall PNN in grey matter of lumbar spinal cord neurons at 3 months post SCI. Notice areas with clear decreased WFA staining of the PNN (asterisk). (C, D) Statistical analyses show the significant reduction of PNN at both L4 and L6/S1 levels in CRP group when compared to the scrambled peptide group. (E, F) Representative higher power immunostaining images of the ventral horn of transverse L4 sections show the strong PNN intensity (arrow) surrounding the NeuN+ cells in scr treated SCI rats (E), while CRP treatment reduces them (F).

FIG. 29 shows that CRP treatment reduced PNN in lumbosacral spinal cord after T8 SCI, and particularly shows the anatomical assessments of perineuronal nets (PNN) in SCI rats. (A, B) Representative L4 spinal cord transverse images show CRP treatment reduces overall PNN in grey matter of lumbar spinal cord neurons at 3 months post SCI. Notice areas with clear decreased WFA staining of the PNN (asterisk). (C, D) Statistical analyses show the significant reduction of PNN at both L4 and L6/S1 levels in CRP group when compared to the scrambled peptide group. (E, F) Representative higher power immunostaining images of the ventral horn of transverse L4 sections show the strong PNN intensity (arrow) surrounding the NeuN+ cells in scr treated SCI rats (E), while CRP treatment reduces them (F). *, P<0.05 when compared to the scr treatment. N=8 per group.

Figure 30:
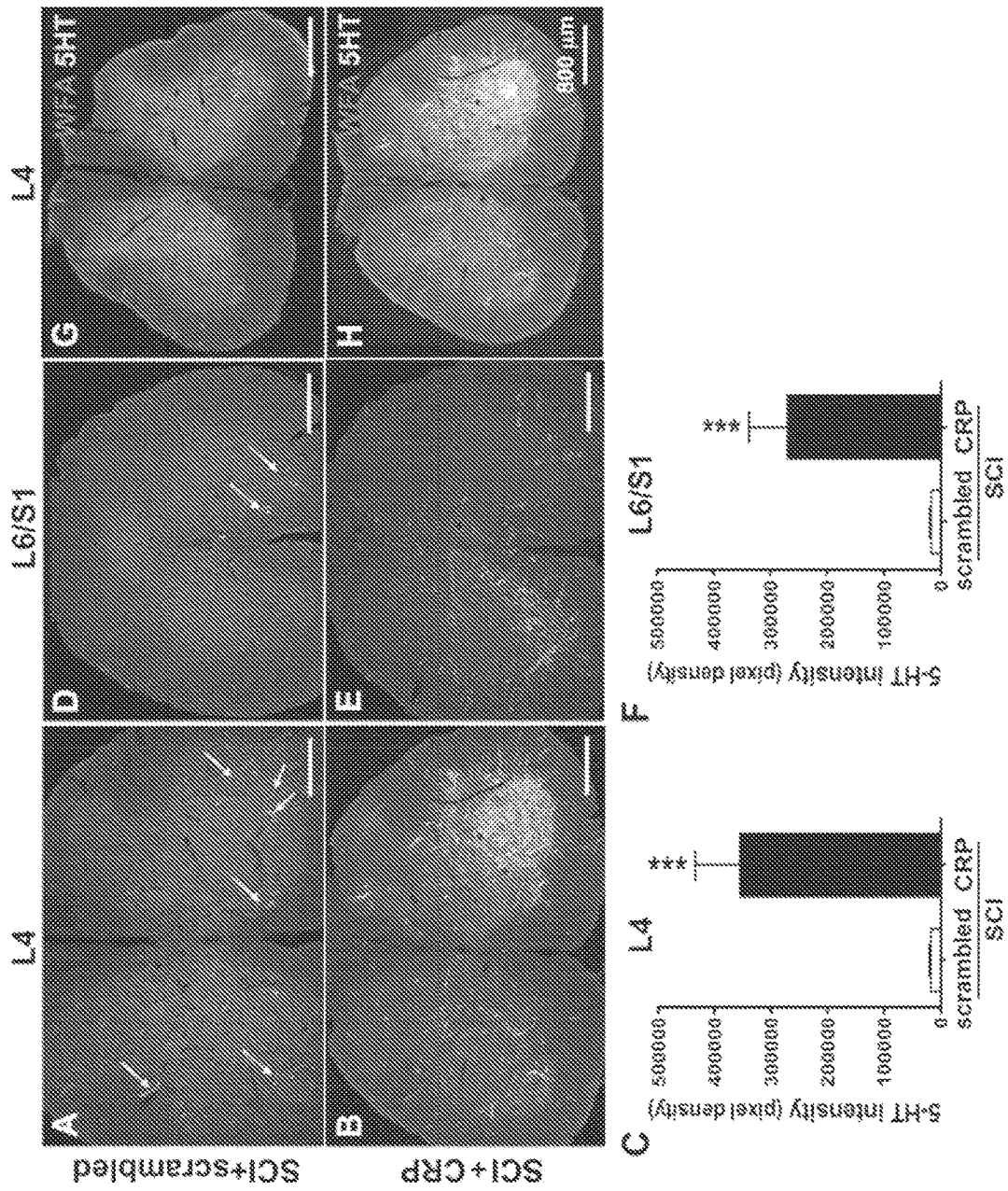
FIG. 30 shows that CRP enhances serotonergic fibers sprouting in lumbrosacral spinal cord. In particular, 5HT immunoreactivity in lumbrosacral level after SCI. (A-F) Representative spinal cord transverse images show that pretty low amount of 5HT fibers (arrow) found at both L4 (A-C) and L6/S1 (D-F) levels after severe contusive SCI, while CRP treatment significantly increases immunoreactivity of 5HT fibers. (G, H) Representative images with double staining of WFA and 5HT showing areas of clear decreased PNN indicated by WFA+, in areas of intense 5-HT sprouting (asterisk).

FIG. 30 shows that CRP enhances serotonergic fibers sprouting in lumbrosacral spinal cord. In particular, 5HT immunoreactivity in lumbosacral level after SCI. (A-F) Representative spinal cord transverse images show that pretty low amount of 5HT fibers (arrow) found at both L4 (A-C) and L6/S1 (D-F) levels after severe contusive SCI, while CRP treatment significantly increases immunoreactivity of 5HT fibers. (G, H) Representative images with double staining of WFA and 5HT showing areas of clear decreased PNN indicated by WFA+, in areas of intense 5-HT sprouting (asterisk). ***, P<0.001 when compared to the scrambled peptide treatment. N=8 per group.

Figure 31:
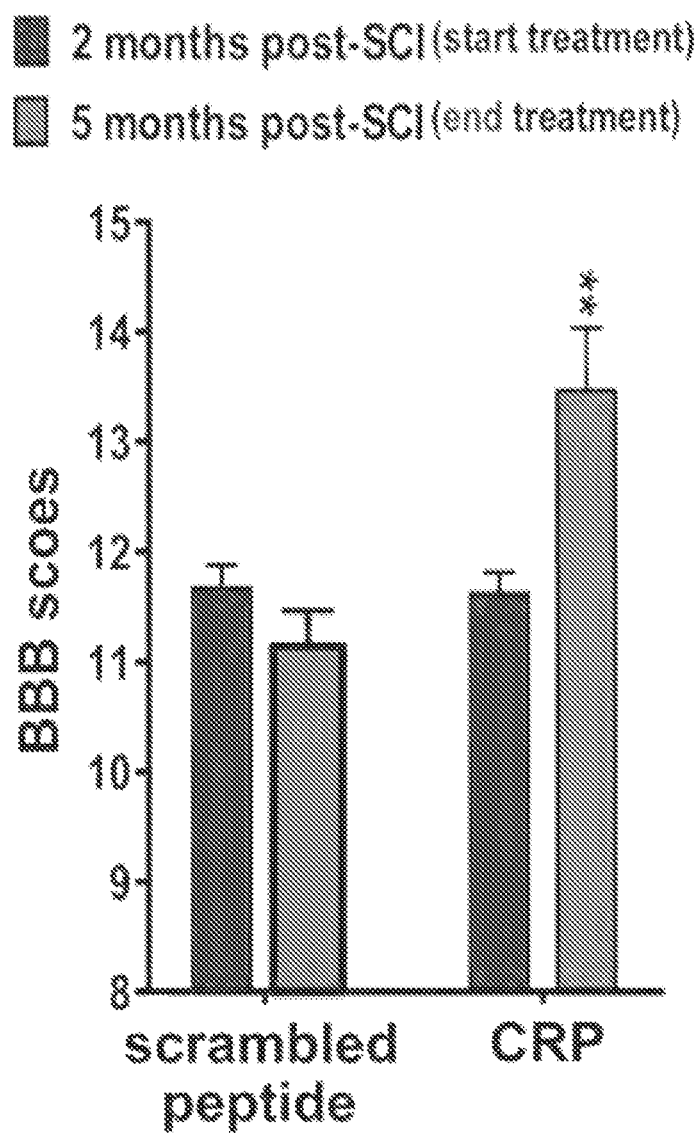
FIG. 31 shows that CRP improves locomotion after chronic SCI. In particular.

FIG. 31 shows that CRP improves locomotion after chronic SCI. In particular, FIG. 31 shows BBB scores that show that CRP treatment improves hindlimb locomotion after chronic SCI (N=6 to 8 animals per group). Note the significant increases in BBB locomotion scale by CRP at 5 months post SCI when compared to what at the time (two months post SCI) of beginning treatment.

Figure 32:
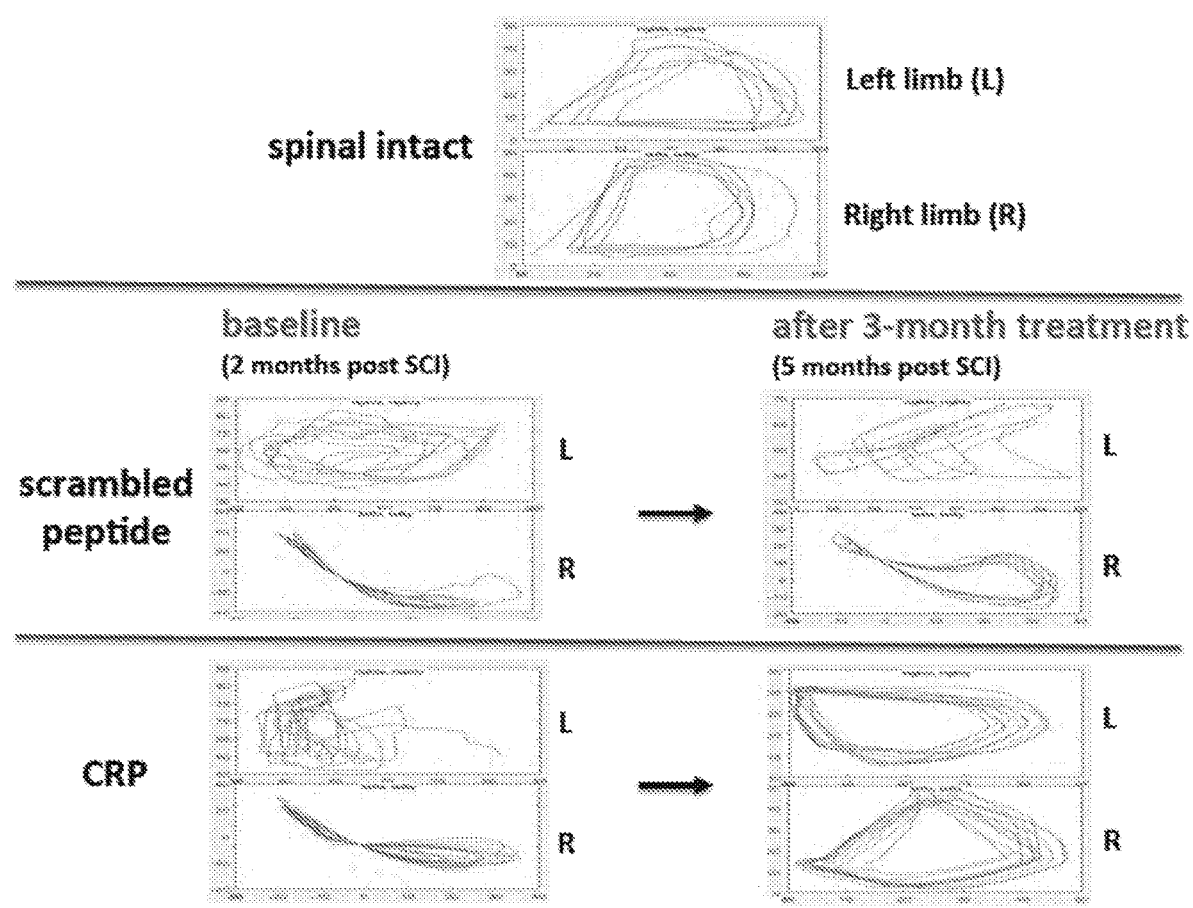
FIG. 32 shows that CRP treatment improves gait patterns after chronic SCI. In particular.

FIG. 32 shows that CRP treatment improves gait patterns after chronic SCI. In particular, FIG. 32 shows representative 2D trajectory patterns indicated CRP treatment improved stepping kinematic of both hindlimbs by CRP at 5 months post SCI when it compared to what at the time (two months post SCI) of beginning treatment.

Figure 33:
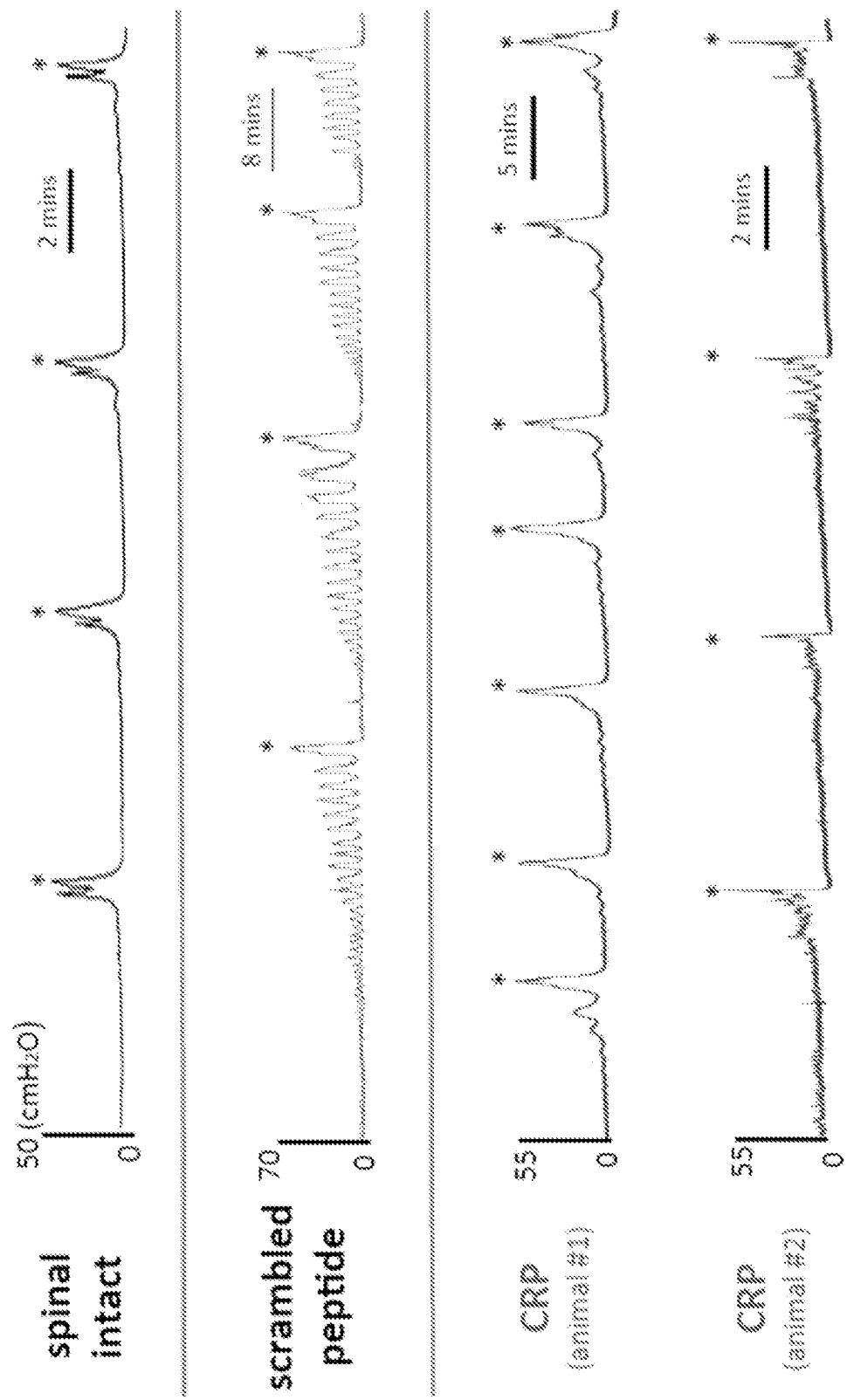
FIG. 33 shows that CRP treatment improves bladder function after chronic SCI. In particular.

FIG. 33 shows that CRP treatment improves bladder function after chronic SCI. In particular, FIG. 33 shows representative cystometrograms (CMG) data indicated 3 months of CRP treatment (starting at 2 months post SCI) can reduce hyperactive bladder and improve other CMG parameters.

Figure 34:
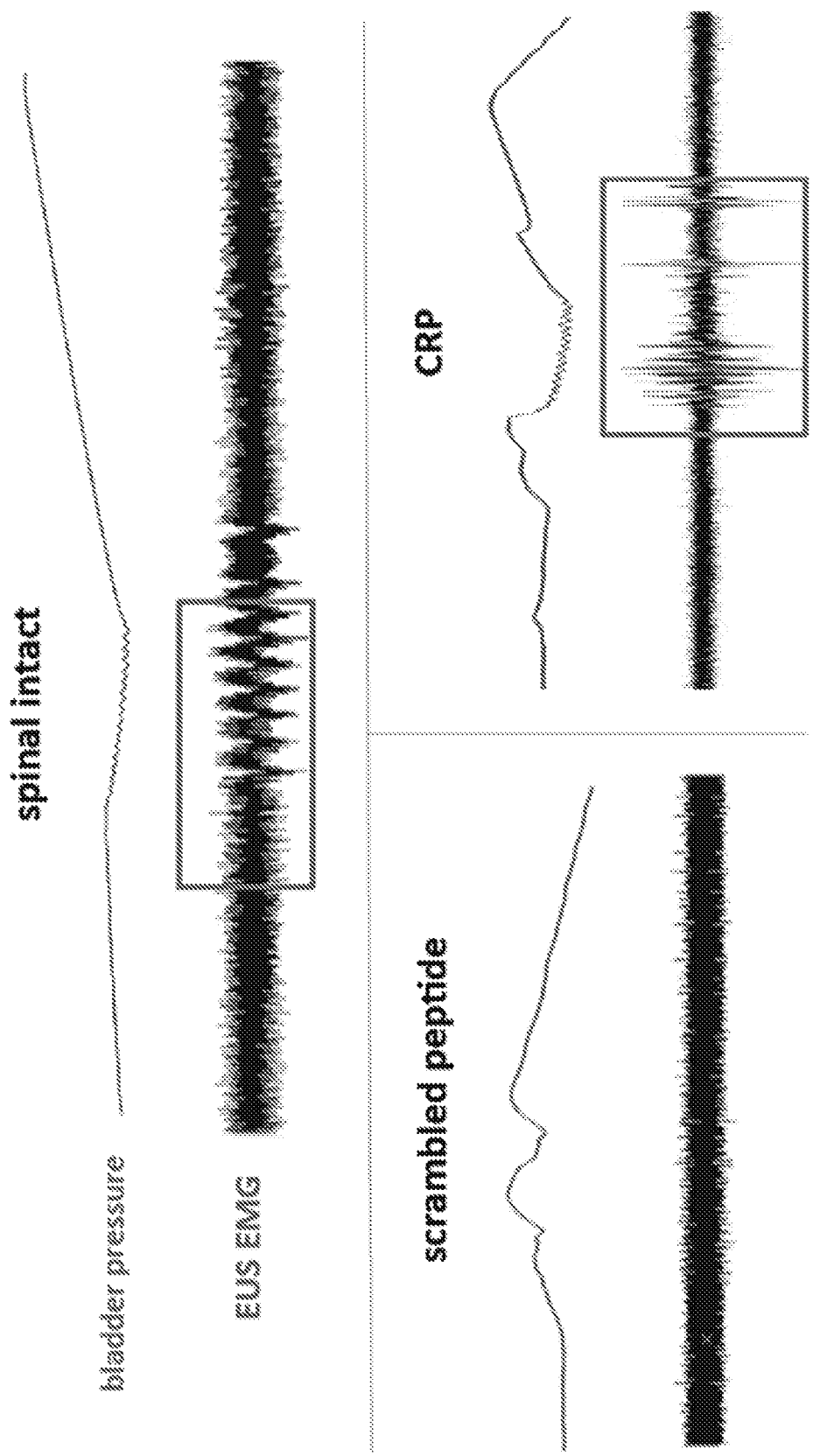
FIG. 34 shows that CRP treatment improves EUS EMG activity during the void after chronic SCI. In particular.

FIG. 34 shows that CRP treatment improves EUS EMG activity during the void after chronic SCI. In particular, FIG. 34 shows representative urodynamic and external urethral sphincter (EUS) electromyogram (EMG) recordings indicated CRP treatment can improve EUS bursting activity during the void period when compared to the scrambled peptide application after chronic SCI. The box area indicates the bursting activity.

Figure 35:
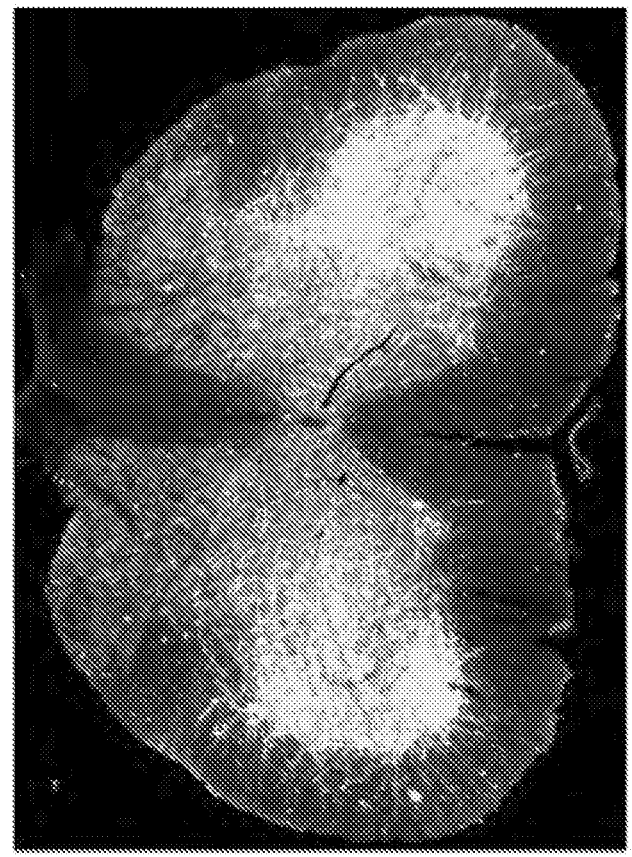
FIG. 35 shows CRP enhances 5HT fibers sprouting in lumbar cord after chronic SCI. In particular.
Figure 35:
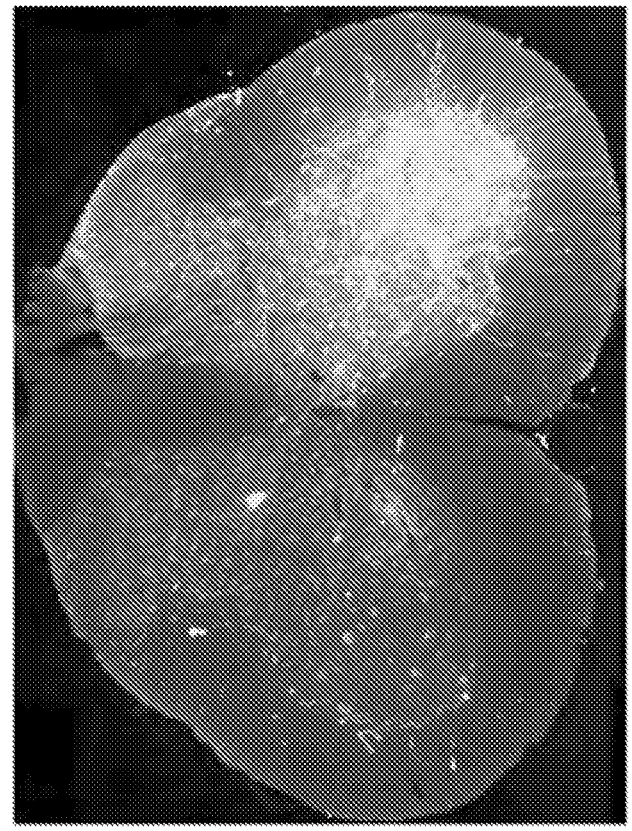

FIG. 35 shows CRP enhances 5HT fibers sprouting in lumbar cord after chronic SCI. In particular, FIG. 35 shows representative spinal cord transverse images that CRP treatment can enhance 5HT+ nerve fibers sprouting in lumbosacral level when compared to the scrambled peptide treatment after chronic SCI.

Figure 36:
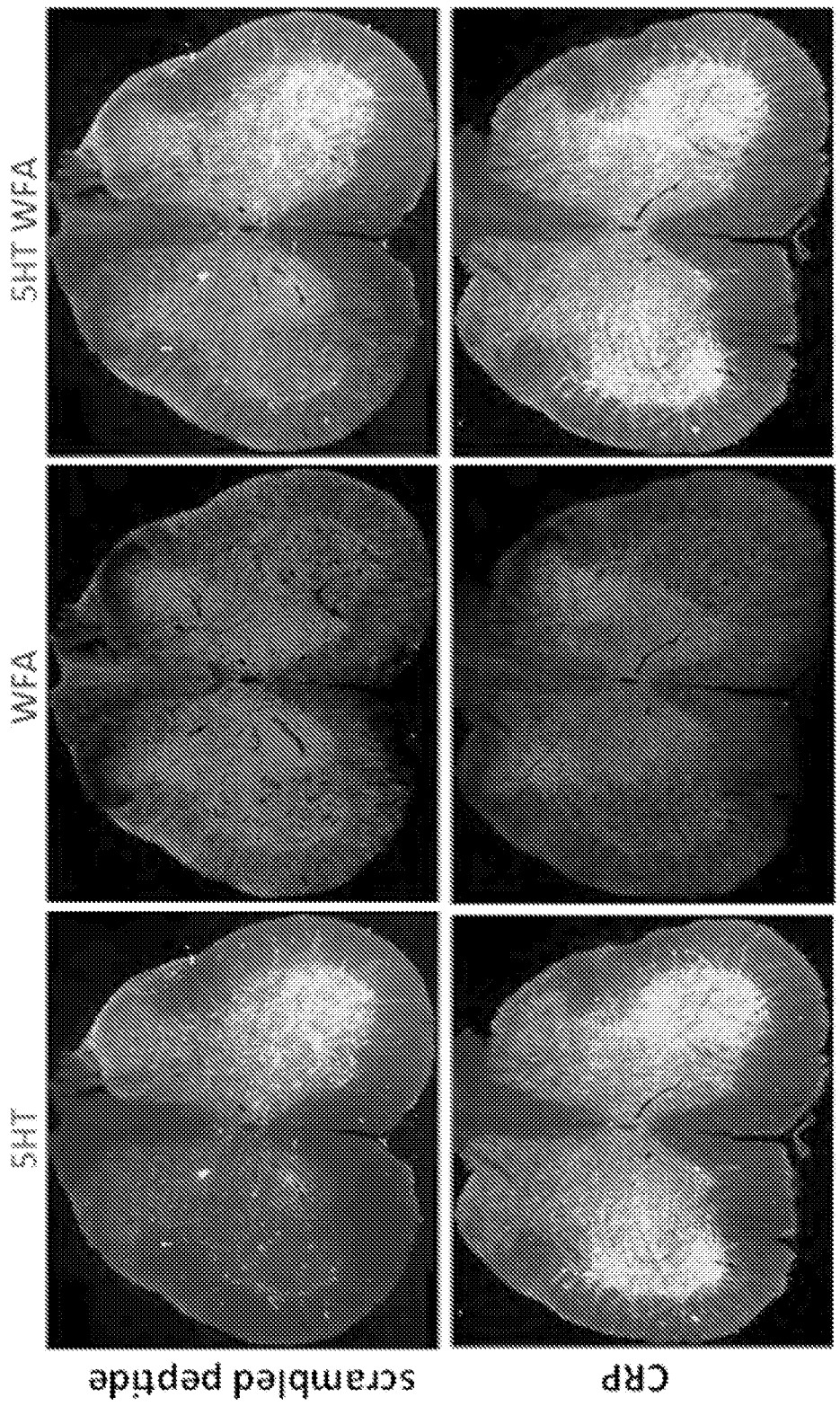
FIG. 36 shows CRP treatment enhances 5HT sprouting but decreases PNN in lumbar cord after chronic SCI. In particular.

FIG. 36 shows CRP treatment enhances 5HT sprouting but decreases PNN in lumbar cord after chronic SCI. In particular, FIG. 36 shows 5HT immunoreactivity in lumbosacral level after chronic SCI. Representative spinal cord transverse images show that low amount of 5HT fibers found at L4 levels after contusive SCI, while CRP treatment significantly increases immunoreactivity of 5HT fibers. Representative images with double staining of WFA and 5HT shows areas with robustly decreased PNN (indicated by WFA+) but enhanced 5-HT sprouting.

Figure 37:
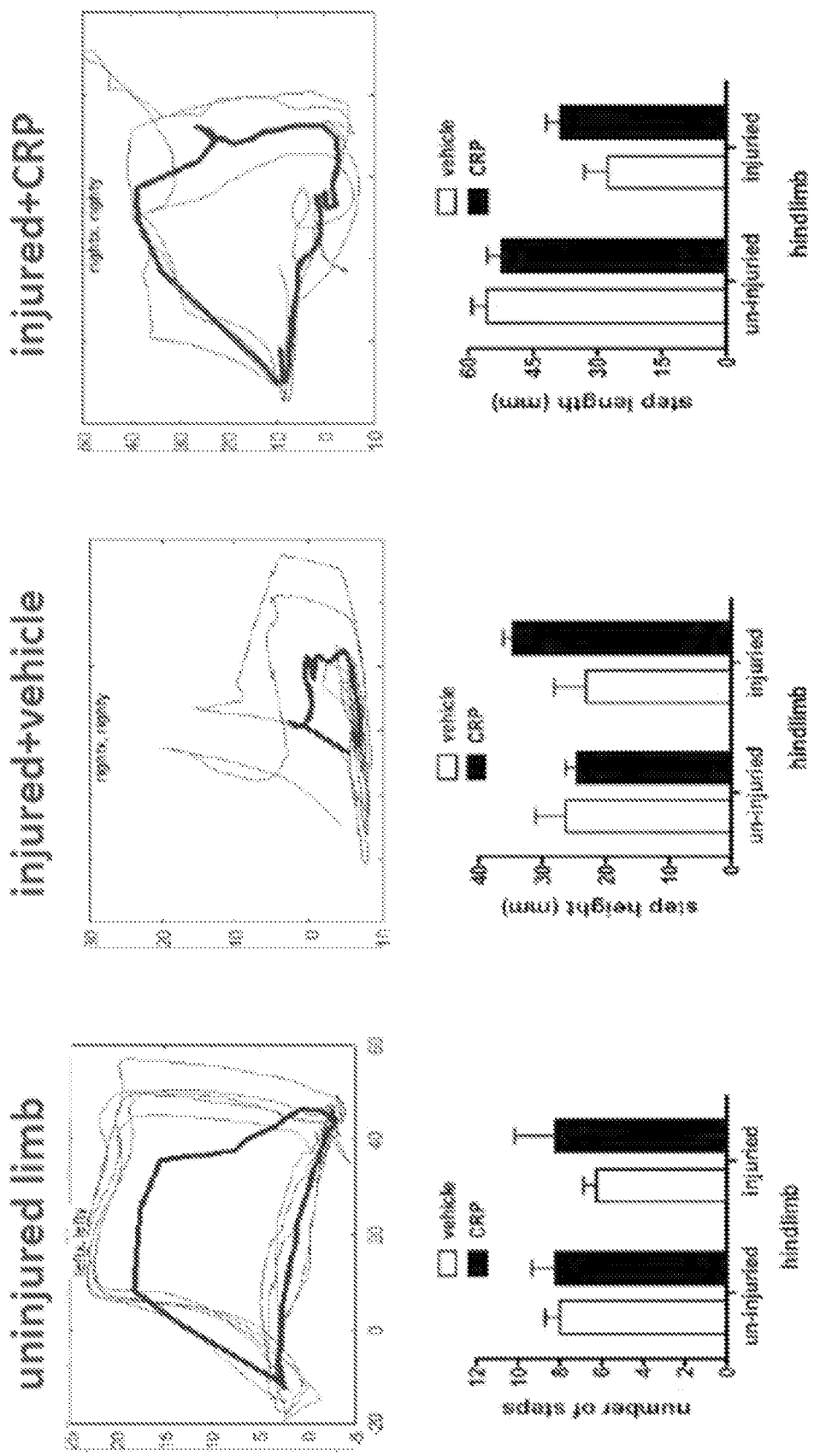
FIG. 37 shows CRP treatment improves gait patterns after sciatic nerve injury. In particular.

FIG. 37 shows CRP treatment improves gait patterns after sciatic nerve injury. In particular, FIG. 37 shows the acute treatment of CRP with allograft of a peripheral nerve segment (2 cm) improved the stepping performance of hindlimbs at 3 months after complete sciatic nerve transection. The representative 2D trajectory and improved kinematics parameters indicated CRP treated animals improved the stepping more toward to what the uninjured limb did, while compared to the vehicle treated animals. The CRP was delivered through subcutaneous injection near the injured site (once per day) staring immediately after surgery for 3 months.

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

We claim:

1. A method of promoting motor function recovery, and/or bladder function recovery, after spinal cord injury in a subject comprising: administering a chondroitin sulfate proteoglycan (CSPG) reduction peptide (CRP), or a nucleic acid sequence encoding said CRP, to a subject with a spinal cord injury, wherein said CRP comprises the amino acid sequence of SEQ ID NO:4.

2. The method of claim 1, wherein said administering is conducted within about 24 hours of said spinal cord injury.

3. The method of claim 1, wherein said administering is conducted after at least two days of said spinal cord injury.

4. The method of claim 1, wherein said administering is conducted at least one week after said spinal cord injury.

5. The method of claim 1, wherein said administering is conducted at least two weeks after said spinal cord injury.

6. The method of claim 1, wherein said administering is conducted at least one month after said spinal cord injury.

7. The method of claim 1, wherein said administering is conducted at least two months after said spinal cord injury.

8. The method of claim 1, wherein said subject has improved motor function after said administering.

9. The method of claim 1, wherein said subject has improved bladder functioning after said administering.

10. A composition comprising a CRP comprising the amino acid sequence of SEQ ID NO:4.

* * * * *

SEQUENCE LISTING

```
<160> NUMBER OF SEQ ID NOS: 90

<210> SEQ ID NO 1
<211> LENGTH: 11
<212> TYPE: PRT
<213> ORGANISM: Artificial Sequence
<220> FEATURE:
<223> OTHER INFORMATION: Synthetic
```

<400> SEQUENCE: 1

Tyr Gly Arg Lys Lys Arg Arg Gln Arg Arg
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic

<400> SEQUENCE: 2

Lys Phe Glu Arg Gln Lys Ile Leu Asp Gln Arg Phe Phe Glu
1               5                   10

<210> SEQ ID NO 3
<211> LENGTH: 19
<212> TYPE: PRT
<213> ORGANISM: Artificial Sequence
<220> FEATURE:
<223> OTHER INFORMATION: Synthetic

<400> SEQUENCE: 3

Pro Lys Pro Arg Val Thr Trp Asn Lys Lys Gly Lys Lys Val Asn Ser
1               5                   10                  15

Gln Arg Phe

<210> SEQ ID NO 4
<211> LENGTH: 46
<212> TYPE: PRT
<213> ORGANISM: Artificial Sequence
<220> FEATURE:
<223> OTHER INFORMATION: Synthetic

<400> SEQUENCE: 4

Asn Tyr Gly Arg Lys Lys Arg Arg Gln Arg Arg Pro Lys Pro Arg
1               5                   10                  15

Val Thr Trp Asn Lys Lys Gly Lys Lys Val Asn Ser Gln Arg Phe Lys
            20                  25                  30

Phe Glu Arg Gln Lys Ile Leu Asp Gln Arg Phe Phe Glu Cys
        35                  40                  45

<210> SEQ ID NO 5
<211> LENGTH: 12
<212> TYPE: PRT
<213> ORGANISM: Artificial Sequence
<220> FEATURE:
<223> OTHER INFORMATION: Synthetic

<400> SEQUENCE: 5

Tyr Gly Arg Lys Lys Arg Arg Gln Arg Arg Cys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic

<400> SEQUENCE: 6

Tyr Gly Arg Lys Lys Arg Arg Gln Arg Arg Gly Cys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic

<400> SEQUENCE: 7

Cys Ala Tyr Gly Arg Lys Lys Arg Arg Gln Arg Arg Arg
1               5                   10

<210> SEQ ID NO 8
<211> LENGTH: 33
<212> TYPE: PRT
<213> ORGANISM: Artificial Sequence
<220> FEATURE:
<223> OTHER INFORMATION: Synthetic

<400> SEQUENCE: 8

Tyr Gly Arg Lys Lys Arg Arg Gln Arg Arg Tyr Gly Arg Lys Lys
1               5                   10                  15

Arg Arg Gln Arg Arg Arg Tyr Gly Arg Lys Lys Arg Arg Gln Arg Arg
            20                  25                  30

Arg

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Gly Arg Lys Lys Arg Arg Gln Arg Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic

<400> SEQUENCE: 10

Gly Arg Lys Lys Arg Arg Gln Arg Arg Arg Gly
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic

<400> SEQUENCE: 11

Gly Arg Lys Lys Arg Arg Gln Arg Arg Arg Cys Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Gly Arg Lys Lys Arg Arg Gln Arg Arg Pro Pro
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic

<400> SEQUENCE: 13

Gly Arg Lys Lys Arg Arg Gln Arg Arg Pro Pro Gln
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic

<400> SEQUENCE: 14

Gly Arg Lys Lys Arg Arg Gln Arg Arg Pro Pro Gln Cys
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Arg Lys Lys Arg Arg Gln Arg Arg Arg
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Arg Lys Lys Arg Arg Gln Arg Arg Arg
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Arg Arg Arg Gln Arg Arg Lys Lys Arg
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

```
Arg Arg Arg Gln Arg Arg Lys Lys Arg
1               5

<210> SEQ ID NO 19
<211> LENGTH: 13
<212> TYPE: PRT
<213> ORGANISM: Artificial Sequence
<220> FEATURE:
<223> OTHER INFORMATION: Synthetic

<400> SEQUENCE: 19

Gly Arg Arg Arg Arg Arg Arg Arg Arg Arg Pro Pro Gln
1               5                   10

<210> SEQ ID NO 20
<211> LENGTH: 19
<212> TYPE: PRT
<213> ORGANISM: Artificial Sequence
<220> FEATURE:
<223> OTHER INFORMATION: Synthetic

<400> SEQUENCE: 20

Thr Arg Gln Ala Arg Arg Asn Arg Arg Arg Trp Arg Glu Arg Gln
1               5                   10                  15

Arg Gly Cys

<210> SEQ ID NO 21
<211> LENGTH: 15
<212> TYPE: PRT
<213> ORGANISM: Artificial Sequence
<220> FEATURE:
<223> OTHER INFORMATION: Synthetic

<400> SEQUENCE: 21

Thr Arg Arg Gln Arg Thr Arg Arg Ala Arg Arg Asn Arg Gly Cys
1               5                   10                  15

<210> SEQ ID NO 22
<211> LENGTH: 21
<212> TYPE: PRT
<213> ORGANISM: Artificial Sequence
<220> FEATURE:
<223> OTHER INFORMATION: Synthetic

<400> SEQUENCE: 22

Lys Leu Thr Arg Ala Gln Arg Arg Ala Ala Ala Arg Lys Asn Lys Arg
1               5                   10                  15

Asn Thr Arg Gly Cys
            20

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Arg Arg Arg Arg Asn Arg Thr Arg Arg Asn Arg Arg Arg Val Arg
1               5                   10                  15

<210> SEQ ID NO 24
<211> LENGTH: 8
<212> TYPE: PRT
<213> ORGANISM: Artificial Sequence
<220> FEATURE:
```

```
<223> OTHER INFORMATION: Synthetic

<400> SEQUENCE: 24

Arg Arg Arg Arg Arg Arg Gly Cys
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic

<400> SEQUENCE: 25

Arg Arg Arg Arg Arg Arg Arg Arg Gly Cys
1               5                   10

<210> SEQ ID NO 26
<211> LENGTH: 21
<212> TYPE: PRT
<213> ORGANISM: Artificial Sequence
<220> FEATURE:
<223> OTHER INFORMATION: Synthetic

<400> SEQUENCE: 26

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 27
<211> LENGTH: 16
<212> TYPE: PRT
<213> ORGANISM: Artificial Sequence
<220> FEATURE:
<223> OTHER INFORMATION: Synthetic

<400> SEQUENCE: 27

Arg Gln Ile Leu Ile Trp Phe Gln Asn Arg Arg Met Lys Trp Lys Lys
1               5                   10                  15

<210> SEQ ID NO 28
<211> LENGTH: 5
<212> TYPE: PRT
<213> ORGANISM: Artificial Sequence
<220> FEATURE:
<223> OTHER INFORMATION: Synthetic

<400> SEQUENCE: 28

Lys Phe Glu Arg Gln
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic

<400> SEQUENCE: 29

Lys Phe Glu Arg Gln
1               5

<210> SEQ ID NO 30
<211> LENGTH: 5
<212> TYPE: PRT
```

```
<213> ORGANISM: Artificial Sequence
<220> FEATURE:
<223> OTHER INFORMATION: Synthetic

<400> SEQUENCE: 30

Gln Lys Ile Leu Asp
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic

<400> SEQUENCE: 31

Gln Arg Phe Phe Glu
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Lys Phe Glu Arg Gln Lys Ile Leu Asp
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic

<400> SEQUENCE: 33

Gln Lys Ile Leu Asp Gln Arg Phe Phe Glu
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Lys Phe Glu Arg Gln Arg Phe Phe Glu
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic

<400> SEQUENCE: 35

Gln Arg Phe Phe Glu Arg Gln
1               5

<210> SEQ ID NO 36
<211> LENGTH: 7
<212> TYPE: PRT
<213> ORGANISM: Artificial Sequence
```

```
<220> FEATURE:
<223> OTHER INFORMATION: Synthetic

<400> SEQUENCE: 36

Gln Arg Lys Phe Glu Arg Gln
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic

<400> SEQUENCE: 37

Lys Lys Gly Lys Lys
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Asn Lys Lys Gly Lys Lys Val
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic

<400> SEQUENCE: 39

Asn Lys Lys Gly Lys Lys Val Asn Ser
1               5

<210> SEQ ID NO 40
<211> LENGTH: 11
<212> TYPE: PRT
<213> ORGANISM: Artificial Sequence
<220> FEATURE:
<223> OTHER INFORMATION: Synthetic

<400> SEQUENCE: 40

Lys Lys Gly Lys Lys Val Asn Ser Gln Arg Phe
1               5                   10

<210> SEQ ID NO 41
<211> LENGTH: 15
<212> TYPE: PRT
<213> ORGANISM: Artificial Sequence
<220> FEATURE:
<223> OTHER INFORMATION: Synthetic

<400> SEQUENCE: 41

Arg Val Thr Trp Asn Lys Lys Gly Lys Lys Val Asn Ser Gln Arg
1               5                   10                  15

<210> SEQ ID NO 42
<211> LENGTH: 20
<212> TYPE: PRT
<213> ORGANISM: Artificial Sequence
<220> FEATURE:
```

<223> OTHER INFORMATION: Synthetic

<400> SEQUENCE: 42

Pro Lys Pro Arg Val Thr Trp Asn Lys Lys Gly Lys Lys Val Asn Ser
1               5                   10                  15

Gln Arg Phe Glu
            20

<210> SEQ ID NO 43
<211> LENGTH: 22
<212> TYPE: PRT
<213> ORGANISM: Artificial Sequence
<220> FEATURE:
<223> OTHER INFORMATION: Synthetic

<400> SEQUENCE: 43

Thr Gly Asp Pro Lys Pro Arg Val Thr Trp Asn Lys Lys Gly Lys Lys
1               5                   10                  15

Val Asn Ser Gln Arg Phe
            20

<210> SEQ ID NO 44
<211> LENGTH: 23
<212> TYPE: PRT
<213> ORGANISM: Artificial Sequence
<220> FEATURE:
<223> OTHER INFORMATION: Synthetic

<400> SEQUENCE: 44

Thr Gly Asp Pro Lys Pro Arg Val Thr Trp Asn Lys Lys Gly Lys Lys
1               5                   10                  15

Val Asn Ser Gln Arg Phe Glu
            20

<210> SEQ ID NO 45
<211> LENGTH: 19
<212> TYPE: PRT
<213> ORGANISM: Artificial Sequence
<220> FEATURE:
<223> OTHER INFORMATION: Synthetic

<400> SEQUENCE: 45

Pro Lys Pro Arg Val Thr Trp Asn Arg Lys Gly Lys Lys Val Asn Ser
1               5                   10                  15

Gln Arg Phe

<210> SEQ ID NO 46
<211> LENGTH: 19
<212> TYPE: PRT
<213> ORGANISM: Artificial Sequence
<220> FEATURE:
<223> OTHER INFORMATION: Synthetic

<400> SEQUENCE: 46

Pro Lys Pro Arg Val Thr Trp Asn Arg Arg Gly Lys Lys Val Asn Ser
1               5                   10                  15

Gln Arg Phe

<210> SEQ ID NO 47
<211> LENGTH: 19
<212> TYPE: PRT
<213> ORGANISM: Artificial Sequence
<220> FEATURE:
<223> OTHER INFORMATION: Synthetic

<400> SEQUENCE: 47

Pro Lys Pro Arg Val Thr Trp Asn Arg Arg Gly Arg Lys Val Asn Ser
1               5                   10                  15

Gln Arg Phe

<210> SEQ ID NO 48
<211> LENGTH: 19
<212> TYPE: PRT
<213> ORGANISM: Artificial Sequence
<220> FEATURE:
<223> OTHER INFORMATION: Synthetic

<400> SEQUENCE: 48

Pro Lys Pro Arg Val Thr Trp Asn Arg Arg Gly Arg Arg Val Asn Ser
1               5                   10                  15

Gln Arg Phe

<210> SEQ ID NO 49
<211> LENGTH: 19
<212> TYPE: PRT
<213> ORGANISM: Artificial Sequence
<220> FEATURE:
<223> OTHER INFORMATION: Synthetic

<400> SEQUENCE: 49

Pro Lys Pro Arg Val Thr Trp Asn Lys Arg Gly Lys Lys Val Asn Ser
1               5                   10                  15

Gln Arg Phe

<210> SEQ ID NO 50
<211> LENGTH: 19
<212> TYPE: PRT
<213> ORGANISM: Artificial Sequence
<220> FEATURE:
<223> OTHER INFORMATION: Synthetic

<400> SEQUENCE: 50

Pro Lys Pro Arg Val Thr Trp Asn Lys Arg Gly Arg Lys Val Asn Ser
1               5                   10                  15

Gln Arg Phe

<210> SEQ ID NO 51
<211> LENGTH: 19
<212> TYPE: PRT
<213> ORGANISM: Artificial Sequence
<220> FEATURE:
<223> OTHER INFORMATION: Synthetic

<400> SEQUENCE: 51

Pro Lys Pro Arg Val Thr Trp Asn Lys Arg Gly Arg Arg Val Asn Ser
1               5                   10                  15

Gln Arg Phe

<210> SEQ ID NO 52
<211> LENGTH: 19
<212> TYPE: PRT
<213> ORGANISM: Artificial Sequence
<220> FEATURE:
<223> OTHER INFORMATION: Synthetic

<400> SEQUENCE: 52

Pro Lys Pro Arg Val Thr Trp Asn Lys Lys Gly Arg Lys Val Asn Ser

Gln Arg Phe

<210> SEQ ID NO 53
<211> LENGTH: 19
<212> TYPE: PRT
<213> ORGANISM: Artificial Sequence
<220> FEATURE:
<223> OTHER INFORMATION: Synthetic

<400> SEQUENCE: 53

Pro Lys Pro Arg Val Thr Trp Asn Lys Lys Gly Arg Arg Val Asn Ser
1               5                   10                  15

Gln Arg Phe

<210> SEQ ID NO 54
<211> LENGTH: 10
<212> TYPE: PRT
<213> ORGANISM: Artificial Sequence
<220> FEATURE:
<223> OTHER INFORMATION: Synthetic

<400> SEQUENCE: 54

Val Gln Pro Tyr Ser Thr Val Val His Ser
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Val Gln Tyr Ser Thr Val Val His Ser
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic

<400> SEQUENCE: 56

Val Glu Pro Tyr Ser Thr Val Val His Ser
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Synthetic

<400> SEQUENCE: 57

Val Glu Tyr Ser Thr Val Val His Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic
<220> FEATURE:

<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 58

Val Xaa Pro Tyr Xaa Xaa Val Val Xaa
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 59

Val Xaa Pro Tyr Xaa Xaa Leu Val Xaa
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 60

Val Xaa Pro Tyr Xaa Xaa Val Leu Xaa
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:

```
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 61

Leu Xaa Pro Tyr Xaa Xaa Val Val Xaa
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 62

Val Xaa Pro Tyr Xaa Xaa Leu Leu Xaa
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 63

Leu Xaa Pro Tyr Xaa Xaa Val Leu Xaa
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
```

```
<221> NAME/KEY: misc_feature
<222> LOCATION: (9)..(9)
<223> OTHER INFORMATION: Xaa can be any naturally occurring amino acid

<400> SEQUENCE: 64

Leu Xaa Pro Tyr Xaa Xaa Leu Val Xaa
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 65

Leu Xaa Pro Tyr Xaa Xaa Leu Leu Xaa
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 66

Val Xaa Tyr Xaa Xaa Val Val Xaa
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
```

<400> SEQUENCE: 67

Val Xaa Tyr Xaa Xaa Leu Val Xaa
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 68

Val Xaa Tyr Xaa Xaa Val Leu Xaa
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 69

Leu Xaa Tyr Xaa Xaa Val Val Xaa
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 70

Val Xaa Tyr Xaa Xaa Leu Leu Xaa
1               5

```
<210> SEQ ID NO 71
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 71

Leu Xaa Tyr Xaa Xaa Val Leu Xaa
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 72

Leu Xaa Tyr Xaa Xaa Leu Val Xaa
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 73

Leu Xaa Tyr Xaa Xaa Leu Leu Xaa
1               5

<210> SEQ ID NO 74
<211> LENGTH: 10
```

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 74

Val Xaa Pro Tyr Xaa Xaa Val Val Xaa Ser
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 75

Val Xaa Pro Tyr Xaa Xaa Leu Val Xaa Ser
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 76

Val Xaa Pro Tyr Xaa Xaa Val Leu Xaa Ser
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 77

Leu Xaa Pro Tyr Xaa Xaa Val Val Xaa Ser
 1               5                  10

<210> SEQ ID NO 78
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 78

Val Xaa Pro Tyr Xaa Xaa Leu Leu Xaa Ser
 1               5                  10

<210> SEQ ID NO 79
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 79

Leu Xaa Pro Tyr Xaa Xaa Val Leu Xaa Ser
 1               5                  10

<210> SEQ ID NO 80
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
```

```
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 80

Leu Xaa Pro Tyr Xaa Xaa Leu Val Xaa Ser
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 81

Leu Xaa Pro Tyr Xaa Xaa Leu Leu Xaa Ser
1               5                   10

<210> SEQ ID NO 82
<211> LENGTH: 16
<212> TYPE: PRT
<213> ORGANISM: Artificial Sequence
<220> FEATURE:
<223> OTHER INFORMATION: Synthetic

<400> SEQUENCE: 82

Ser Thr Ala Ser Thr Val Glu Pro Tyr Ser Thr Val Val His Ser Gly
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic

<400> SEQUENCE: 83

Ser Thr Ala Ser Thr Val Glu Pro Tyr Ser Thr Val Val His Ser
1               5                   10                  15

<210> SEQ ID NO 84
<211> LENGTH: 14
<212> TYPE: PRT
<213> ORGANISM: Artificial Sequence
<220> FEATURE:
<223> OTHER INFORMATION: Synthetic

<400> SEQUENCE: 84

Ser Thr Ala Ser Thr Val Gln Pro Tyr Ser Thr Val Val His
1               5                   10
```

```
<210> SEQ ID NO 85
<211> LENGTH: 13
<212> TYPE: PRT
<213> ORGANISM: Artificial Sequence
<220> FEATURE:
<223> OTHER INFORMATION: Synthetic

<400> SEQUENCE: 85

Ser Thr Ala Ser Thr Val Gln Pro Tyr Ser Thr Val Val
1               5                   10

<210> SEQ ID NO 86
<211> LENGTH: 16
<212> TYPE: PRT
<213> ORGANISM: Artificial Sequence
<220> FEATURE:
<223> OTHER INFORMATION: Synthetic

<400> SEQUENCE: 86

Ser Thr Ala Ser Thr Val Gln Pro Tyr Ser Thr Val Val His Ser Gly
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic

<400> SEQUENCE: 87

Ser Thr Ala Ser Thr Val Gln Pro Tyr Ser Thr Val Val His Ser
1               5                   10                  15

<210> SEQ ID NO 88
<211> LENGTH: 14
<212> TYPE: PRT
<213> ORGANISM: Artificial Sequence
<220> FEATURE:
<223> OTHER INFORMATION: Synthetic

<400> SEQUENCE: 88

Ser Thr Ala Ser Thr Val Gln Pro Tyr Ser Thr Val Val His
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetic

<400> SEQUENCE: 89

Ser Thr Ala Ser Thr Val Gln Pro Tyr Ser Thr Val Val
1               5                   10

<210> SEQ ID NO 90
<211> LENGTH: 35
<212> TYPE: PRT
<213> ORGANISM: Artificial Sequence
<220> FEATURE:
<223> OTHER INFORMATION: Synthetic

<400> SEQUENCE: 90

Tyr Gly Arg Lys Lys Arg Arg Gln Arg Arg Val Gln Pro Tyr Ser
1               5                   10                  15
```

```
Thr Val Val His Ser Lys Phe Glu Arg Gln Lys Ile Leu Asp Gln Arg
            20                  25                  30

Phe Phe Glu
        35
```